(12) United States Patent
Yi et al.

(10) Patent No.: US 8,435,472 B2
(45) Date of Patent: May 7, 2013

(54) METHOD OF PREPARING NANO-STRUCTURED MATERIAL(S) AND USES THEREOF

(75) Inventors: Guang-Shun Yi, Singapore (SG); Gan-Moog Chow, Singapore (SG)

(73) Assignee: National University of Singapore, Singapore (SG)

( * ) Notice: Subject to any disclaimer, the term of this patent is extended or adjusted under 35 U.S.C. 154(b) by 1309 days.

(21) Appl. No.: 12/087,414

(22) PCT Filed: Jan. 5, 2007

(86) PCT No.: PCT/SG2007/000003
§ 371 (c)(1),
(2), (4) Date: Jul. 3, 2008

(87) PCT Pub. No.: WO2007/078262
PCT Pub. Date: Jul. 12, 2007

(65) Prior Publication Data
US 2009/0081461 A1 Mar. 26, 2009

Related U.S. Application Data

(60) Provisional application No. 60/756,557, filed on Jan. 6, 2006.

(51) Int. Cl.
*C01F 1/00* (2006.01)
(52) U.S. Cl.
USPC .......................... 423/263; 423/21.1; 423/274
(58) Field of Classification Search .................. 423/21.1, 423/263, 274, 155, 179
See application file for complete search history.

(56) References Cited

U.S. PATENT DOCUMENTS 5,674,698 A 10/1997 Zarling et al.
6,574,039 B1 * 6/2003 Murata et al. .................. 359/359

FOREIGN PATENT DOCUMENTS

WO  WO 94/07142 A1  3/1994
WO  WO 2005/015213  2/2005

OTHER PUBLICATIONS

Mai, et al., "High-quality sodium rare-earth fluoride nanocrystals: controlled synthesis and optical properties" J. American Chemical Soc. Apr. 20, 2006, 128, pp. 6426-6436.*
Ya-Wen Zhang et al., "Single-Crystalline and Monodisperse LaF3 Triangular Nanoplates from a Single-Source Precursor", Journal of the American Chemical Society, Feb. 17, vol. 27, No. 10, pp. 3260-3261.
S. Tanabe et al., "Fluorescence Properties of $Er^{3+}$ Ions in Glass Ceramics Containing $LaF_3$ Nanocrystals", Optical Materials, vol. 19, pp. 343-349, 2002.
G. Yi et al., "Synthesis, Characterization, and Biological Application of Size-Controlled Nanocrystalline $NaYF_4$:Yb,Er Infrared-to-visible Up-Conversion Phosphors", Nano Letters, vol. 4, No. 11, pp. 2191-2196, 2004.
R. Yan et al., "Down/Up Conversion in $Lu^{3+}$-Doped $YF_3$ Nanocrystals", Advanced Functional Materials, vol. 15, No. 5, pp. 763-770, May 2005.
G. Blasse et al., "Luminescent Materials," Springer, Berlin, 5pgs. (1994).
M. Bruchez, Jr. et al., "Semiconductor Nanocrystals as Fluorescent Biological Labels," Science, vol. 281, No. 5385, pp. 2013-2016, Sep. 25, 1998.
X. Y. Chen et al., "Confinement on Energy Transfer Between Luminescent Centers in Nanocrystals," Journal of Applied Physics, vol. 94, No. 9, pp. 5559-5565, Nov. 1, 2003.
P.L.A.M. Corstjens et al., "Infrared Up-Converting Phospors for Bioassays," IEE Proc.—Nanobiotechnol., vol. 152, No. 2, pp. 64-72, Apr. 2, 2005.
B. Dubertret et al., "In Vivo Imaging of Quantum Dots Encapsulated in Phospholipid Micelles," Science, vol. 298, pp. 1759-1762, Nov. 29, 2002.
D. Gerion et al., "Synthesis and Properties of Biocompatible Water-Soluble Silica-Coated CdSe/ZnS Semiconductor Quantum Dots," J. Phys. Chem. B, vol. 105, No. 37, pp. 8861-8871, 2001.
S. Heer et al., "Highly Efficient Multicolour Upconversion Emission in Transparent Colloids of Lanthanide-Doped $NaYF_4$ Nanocrystals," Adv. Mater., vol. 16, No. 23-24, pp. 2102-2105, Dec. 17, 2004.
S. Heer et al., "Blue, Green, and Red Upconversion Emission from Lanthanide-Doped $LuPO_4$ and $YbPO_4$ Nanocrystals in a Transparent Colloidal Solution," Angew. Chem. Int. Ed., vol. 42, pp. 3179-3182, 2003.
F. van de Rijke et al., " Up-Converting Phosphor Reporters for Nucleic Acid Microarrays, " Nature Biotechnology, vol. 19, pp. 273-276, Mar. 2001.
X. Wang et al., "A General Strategy for Nanocrystal Synthesis," Nature, vol. 437, pp. 121-124, Sep. 1, 2005.
G-S Yi et al., "Colloidal $LaF_3$: Yv,Er, $LaF_3$:Yb,Ho and $LaF_3$:Yb,Tm Nanocrystals with Mulitcolor Upconversion Fluorescence," Journal of Materials Chemistry, vol. 15, pp. 4460-4464, 2005.
J-H Zeng et al., "Synthesis and Upconversion Luminescence of Hexagonal-Phase $NaYF_4$:Yb, $Er^{3+}$ Phosphors of Controlled Size and Morphology," Advanced Materials, vol. 17, pp. 2119-2123, 2005.
V. Sudarsan et al., General and Convenient Method for Making Highly Luminescent Sol-Gel Derived Silica and Alumina Films by Using $LaF_3$Nanoparticles Doped with Lanthanide Ions ($Er^{3+}$, $Nd^{3+}$, and $Ho^{3+}$). Chem. Mater., vol. 17, No. 18, pp. 4736-4742, 2005.

* cited by examiner

Primary Examiner — Steven Bos
(74) Attorney, Agent, or Firm — Dickstein Shapiro LLP

(57) ABSTRACT

The present invention provides a method of preparing at least one nano-structured material of formula $M_1M_2X_n$ comprising the step of treating: at least one compound having the formula $[CX_3(CX_2)_n(CH_2)_mCOO]_pM_1$; and at least one compound having the formula $[CX_3(CX_2)_n(CH_2)_mCOO]_pM_2$; wherein each X is the same or different and is selected from the group consisting of: halogens, O, S, Se, Te, N, P and As; each n is the same or different and is $0 \leq n \leq 10$; each m is the same or different and is $0 \leq m \leq 10$; each p is the same or different and is $1 \leq p \leq 5$; each $M_1$ is the same or different and is selected from the group consisting of: Li, Na, K, Rb, Cs, Fr, Be, Mg, Ca, Sr, Ba, Ra and $NH_4$; each $M_2$ is the same or different and is a metal ion. The present invention also provides uses of the nano-structured material prepared according to the method of the present invention.

17 Claims, 22 Drawing Sheets

(a)

(b)

(a)

(b)

(a)

(b)

(a)

(b)

(a)

(b)

SEQUENCE LISTING

<160> NUMBER OF SEQ ID NOS: 1

<210> SEQ ID NO 1
<211> LENGTH: 9
<212> TYPE: PRT
<213> ORGANISM: Artificial
<220> FEATURE:
<223> OTHER INFORMATION: 925 to 933 laminin fragment

<400> SEQUENCE: 1

Cys Asp Pro Gly Tyr Ile Gly Ser Arg
1               5

METHOD OF PREPARING NANO-STRUCTURED MATERIAL(S) AND USES THEREOF

This application claims the benefit of U.S. Provisional Application No. 60/756,557, filed Jan. 6, 2006.

FIELD OF THE INVENTION

The present invention relates to nano-structured materials and a method of preparing the nano-structured materials. The present invention also provides uses of the prepared nano-structured materials.

BACKGROUND OF THE INVENTION

The search for ultra sensitive fluorescent bio-probes for analytical and biophysical applications is very active (Bruchez M. et al, 1998; van de Rijke et al, 2001). To date, the commonly used fluorescent bio-probes are organic dyes, such as rhodamine, fluorescein isothiocyanates (FITC), and cyanine dyes (Cy3, Cy5 and Cy7). More recently, semiconductor nanoparticles (quantum dots, QDs) have been employed as bio-probes (Gerion D et al, 2001; Dubertret B et al, 2002). These down-conversion fluorescent bio-probes emit one lower energy fluorescent photon after absorbing another higher energy UV or visible photon. The main problem of these probes in bio-applications is the autofluorescence (noise) from the analytes under UV and visible light. It decreases the signal-to-noise ratio, limiting the sensitivity.

The use of infrared-to-visible up-conversion phosphors as bio-probe, which is able to absorb and combine two or more near-infrared (NIR) photons with lower energy to produce a higher energy photon in the visible spectrum, is a promising approach to solve the problem of autofluorescence. This concept was first disclosed in U.S. Pat. No. 5,674,698. Compared with the current bio-probes including organic dyes, fluorescent proteins and quantum dots, the advantages include: improved signal-to-noise ratio due to absence of autofluorescence and reduction of light scattering, the non-invasive 980 nm NIR excitation falls within the "water window" (a gap in the absorption spectrum of tissue between chromophores (<800 nm) and water (>1200 nm)). In vivo imaging can be easily achieved as a function of the strong tissue penetration ability of the NIR. Photo-bleaching can be greatly reduced because of the resistance to photo-bleaching of these inorganic nanoparticles. Multiple labelling can also be achieved by the fluorescent nanoparticles at various optical wavelengths under the same 980 nm NIR excitation.

Currently, the fabrication of up-conversion fluorescent inorganic nanoparticles suitable as bio-probe remains as the key technological issue. As bio-probes, the targeted molecules (such as proteins, oligonucleotides and other biomolecules in cells or tissues) are in the range from several nanometers to tens of nanometers. An optimal universal bio-probe therefore should be small in size with narrow size distribution. It should yield high fluorescent efficiency and must be water re-dispersible (Dubertret B et al, 2002).

The most efficient infrared-to-visible up-conversion phosphors are Yb—Er or Yb—Tm co-doped fluorides such as $NaYF_4$, $BaYF_5$, $NaLaF_4$, $NaGdF_4$, $YF_3$, $LaF_3$, $GdF_3$ and oxysulphides like $Y_2O_2S$ (Basse G and Grabmaier B C, 1994), where fluorides and oxysulphide are the hosts, ytterbium (Yb) acts as the sensitizer and erbium (Er) or thulium (Tm) acts as the fluorescent centre. Under the 980 nm NIR excitation, they give off different colours of visible up-conversion fluorescence, depending on the different doping ions. Among them, rare earth doped hexagonal phase $NaYF_4$ is one of the most efficient material for green and blue up-conversion. However, all these commercially available phosphors are in bulk form usually prepared by high-temperature solid-state reactions. Making these bulk phosphors into nanoparticles, which simultaneously satisfy the bio-probe criteria mentioned above, remains a big challenge. Several research groups have sought alternative approaches and synthesized the up-conversion fluorescent nanoparticles for bio-probes. 400 nm Yb—Er and Yb—Tm co-doped $Y_2O_2S$ up-conversion fluorescent particles have been adopted for detection of nucleic acid (van de Rijke, F et al, 2001). The particles were prepared using the method disclosed in U.S. Pat. No. 6,039,894. Their synthesized particles were, however, too large for application as bio-probes; and the efficiency of $Y_2O_2S$ was less than that of the hexagonal phase $NaYF_4$ phosphors. Fabrication of smaller particles is being researched on (Corstjens P et al. 2005). Several other research groups focused on the synthesis of doped $NaYF_4$ nanoparticles.

In WO 03/087259 the synthesis of 37 nm $NaYF_4$:Yb,Er up-conversion nanoparticles, by the room-temperature reaction of rare earth-EDTA complex with sodium fluoride in aqueous solution has been disclosed (Yi G S et al, 2004). The synthesis and multicolour up-conversion emission of Yb—Er and Yb—Tm co-doped $NaYF_4$ nanoparticles has been reported (Heer S, et al, 2004). The 15 nm nanoparticles were acquired by the reaction of rare earth N-(2-hydroxyethyl) ethylenediamine salt, sodium alkoxide of N-(2-hydroxyethyl)ethylenediamine and N-(2-hydroxyethyl)ethylenediamine fluoride at 200° C. under dry $N_2$ atmosphere for 2 h. Recently, Wang et al, 2005, reported a liquid-solid-solution (LSS) method for the synthesis of $NaYF_4$:Yb,Er up-conversion nanoparticles. However, all of the above efforts produced cubic-phase nanoparticles, with efficiency of at least one order of magnitude less than the desirable hexagonal phase. Although Zeng J H et al, 2005, reported the synthesis of hexagonal phase NaYF4:Yb,Er(Tm) nanoparticles, the bigger size of approximately 50 nm was not sufficiently small for them to be used as bio-probes for smaller molecules.

Yi G S and Chow G M, 2005, described the synthesis of $LaF_3$:Yb,Er, $LaF_3$:Yb,Ho and $LaF_3$:Yb,Tm nanoparticles of size 5.4 nm having potential applications as bio-probes, by reacting $LaCl_3$, $YbCl_3$, $ErCl_3/HoCl_3/TmCl_3$ and NaF at a temperature of 72° C. The particles could be dispersed in organic solutions and formed a transparent colloid. With the 980 nm NIR excitation, the nanoparticles yielded different fluorescent emissions in the visible range. However, their up-conversion fluorescent was not efficient.

Accordingly, there is a need in this field of technique of improved fluorescent nano-structured materials.

SUMMARY OF THE INVENTION

The present invention addresses the problems above, and in particular provides a method for the preparation of nano-structured material(s). The nano-structured material prepared from the method of the present invention may be used for applications such as in bio-imaging and bio-detection of bio-molecules.

According to a first aspect, the present invention provides a method of preparing at least one nano-structured material of formula $M_1M_2X_t$ comprising the step of treating:

at least one compound having the formula $[CX_3(CX_2)_n(CH_2)_mCOO]_pM_1$; and at least one compound having the formula $[CX_3(CX_2)_n(CH_2)_mCOO]_pM_2$;

wherein
each X is the same or different and is selected from the group consisting of: halogens, O, S, Se, Te, N, P and As;
$0 < t \leq 10$;
each n is the same or different and is $0 \leq n \leq 10$;
each m is the same or different and is $0 \leq m \leq 10$;
each p is the same or different and is $1 \leq p \leq 5$;
each $M_1$ is the same or different and is selected from the group consisting of: Li, Na, K, Rb, Cs, Fr, Be, Mg, Ca, Sr, Ba, Ra and $NH_4$;
each $M_2$ is the same or different and is a metal ion.

According to a particular aspect, the present invention provides a method for preparing at least one nano-structured material of formula $M_1M_2X_t:M_q$ comprising the step of treating:
at least one compound having the formula $[CX_3(CX_2)_n(CH_2)_mCOO]_pM_1$;
at least one compound having the formula $[CX_3(CX_2)_n(CH_2)_mCOO]_pM_2$; and
at least one compound having the formula $[CX_3(CX_2)_n(CH_2)_mCOO]_pM_q$,
wherein
each $M_q$ is the same or different and is selected from the group consisting of Sc, Y, La, Ce, Pr, Nd, Pm, Sm, Eu, Gd, Tb, Dy, Ho, Er, Tm, Yb and Lu;
t, n, m, p, X, $M_1$ and $M_2$ are as defined above; and
each q is the same or different and is $0 \leq q \leq 10$.

According to a further aspect, the treating in the method may be carried out in the presence of at least one source of energy. Any suitable source of energy may be used. For example, the source of energy may be, but not limited to, any one of the following: light source, electric source, thermal source, magnetic source, or a combination thereof. In particular, the source of energy is a thermal source. The treating may be carried out at a temperature of up to about 1000° C. For example, the treating may be carried out at a temperature of 200° C.-400° C. In particular, the treating is carried out at a temperature of 300° C.-350° C. Even more in particular, the treating is carried out at a temperature of 330° C.

According to another aspect, the present invention provides a method of preparing at least one nano-structured material of formula $M_2X_t$ comprising the step of treating at least one compound having the formula $[CX_3(CX_2)_n(CH_2)_mCOO]_pM_2$, in the presence of at least one source of energy, wherein
each X is the same or different and is selected from the group consisting of: halogens, O, S, Se, Te, N, P and As;
$0 < t \leq 10$;
each n is the same or different and is $0 \leq n \leq 10$;
each m is the same or different and is $0 \leq m \leq 10$;
each p is the same or different and is $1 \leq p \leq 5$; and
each $M_2$ is the same or different and is a metal ion.

According to another particular aspect, the present invention provides a method for preparing at least one nano-structured material of formula $M_2X_t:M_q$ comprising the step of treating:
at least one compound having the formula $[CX_3(CX_2)_n(CH_2)_mCOO]_pM_2$, and
at least one compound having the formula $[CX_3(CX_2)_n(CH_2)_mCOO]_pM_q$;
in the presence of at least one source of energy, wherein
each $M_q$ is the same or different and is selected from the group consisting of Sc, Y, La, Ce, Pr, Nd, Pm, Sm, Eu, Gd, Tb, Dy, Ho, Er, Tm, Yb and Lu;
t, n, m, p, X and $M_2$ are as defined above; and
each q is the same or different and is $0 \leq q \leq 10$.

Any suitable source of energy may be used. For example, the source of energy may be, but not limited to, any one of the following: light source, electric source, thermal source, magnetic source or a combination thereof. In particular, the source of energy is a thermal source. The treating may be carried out at a temperature of up to about 1000° C. For example, the treating may be carried out at a temperature of 200° C.-400° C. In particular, the treating is carried out at a temperature of 300° C.-350° C. Even more in particular, the treating is carried out at a temperature of 330° C.

$M_2$, according to any aspect of the present invention, may be the same or different and may be selected from the group consisting of: transition metal ions, inner transition metal ions, and Group I to Group VI metal ions. In particular, each $M_2$ may be the same or different and may be Sc, Y, La, Ce, Pr, Nd, Pm, Sm, Eu, Gd, Tb, Dy, Ho, Er, Tm, Yb or Lu.

The nano-structured material according to any aspect of the present invention may be selected from the group consisting of: $NaM_2F_4$, $LiM_2F_4$, $KM_2F_4$, $RbM_2F_4$, $CsM_2F_4$, $BeM_2F_5$, $Be(M_2)_2F_8$, $MgM_2F_5$, $Mg(M_2)_2F_8$, $CaM_2F_5$, $Ca(M_2)_2F_8$, $SrM_2F_5$, $Sr(M_2)_2F_8$, $BaLnF_5$, $Ba(M_2)_2F_8M_2F_3$, $M_2F_3$, $M_2Cl_3$, $M_2Br_3$, $M_2I_3$, $M_2FClBr$, $M_2OF$, $M_2OCl$, $M_2OBr$, $M_2OS$, $(M_2)_2S_3$, wherein each $M_2$ is as defined above. In particular, the nano-structured material is $NaYF_4$, $LiYF_4$, $BaYF_5$, $NaLaF_4$, $LaF_3$, $YF_3$, $BaY_2F_8$, $NaGdF_4$ or $GdF_3$. Even more in particular, the nano-structured material is $NaYF_4$.

The at least one compound of formula $[CX_3(CX_2)_n(CH_2)_mCOO]_pM_1$ may be selected from the group consisting of: $CF_3COONa$ and $CF_3COOLi$. The at least one compound of formula $[CX_3(CX_2)_n(CH_2)_mCOO]_pM_2$ may be selected from the group consisting of: $(CF_3COO)_3Y$ and $(CF_3COO)_3La$. For example, the at least one compound of formula $[CX_3(CX_2)_n(CH_2)_mCOO]_pM_q$ may be selected from the group consisting of: $(CF_3COO)_3Yb$, $(CF_3COO)_3Er$, $(CF_3COO)_3Tm$ and $(CF_3COO)_3Ho$.

The at least one nano-structured material prepared according to any method of the present invention may be selected from the group consisting of: $NaM_2F_4:M_q$, $LiM_2F_4:M_q$, $KM_2F_4:M_q$, $RbM_2F_4:M_q$, $CsM_2F_4:M_q$, $BeM_2F_5:M_q$, $Be(M_2)_2F_8:M_q$, $MgM_2F_5:M_q$, $Mg(M_2)_2F_8:M_q$, $CaM_2F_5:M_q$, $Ca(M_2)_2F_8:M_q$, $SrM_2F_5:M_q$, $Sr(M_2)_2F_8:M_q$, $BaM_2F_5:M_q$, $Ba(M_2)_2F_8:M_q$, $M_2F_3:M_q$, $M_2Cl_3:M_q$, $M_2Br_3:M_q$, $M_2I_3:M_q$, $M_2FClBr:M_q$, $M_2OF:M_q$, $M_2OCl:M_q$, $M_2OBr:M_q$, $M_2OS:M_q$, $(M_2)_2S_3:M_q$, wherein each $M_2$ and $M_q$ are as defined above. In particular, each $M_q$ is the same or different and is selected from the group consisting of: Yb, Er, Tm and Ho. In particular, the at least one nano-structured material of formula $M_1M_2X_t:M_q$ is $NaYF_4:Yb,Er$; $NaYF_4:Yb,Tm$; $NaYF_4:Yb,Ho$; $LiYF_4:Yb,Er$; $BaYF_5:Yb,Er$; $NaLaF_4:Yb,Er$; or $YOF:Yb,Er$. Even more in particular, the nano-structured material is $NaYF_4:Yb,Er$, $NaYF_4:Yb,Tm$ or $NaYF_4:Yb,Ho$.

According to a further aspect, the mixing or treating in the method according to any aspect of the present invention may be carried out in the presence of at least one polar or non-polar solvent, or a mixture thereof. Any suitable polar or non-polar solvent may be used. For example, the polar solvent may be water, methanol, ethanol, propyl alcohol, butanol, pentanol, hexanol, ketone, ethylene glycol, glycerol, propylene glycol, polyethylene glycol, ethyl acetate and a combination thereof. The non-polar solvent may be oleylamine, octadecene, oleic acid, alkyl amine, dialkyl amine, trialkyl amine, alkenyl amine, dialkenyl amine, trialkenyl amine, alkyl acid, alkenyl acid, trialkyl phosphine, trialkyl phosphine oxide, trialkylphosphate, alkane, alkene, alkyl ether, alkenyl ether or a combination thereof.

The at least one nano-structured material prepared by the method according to any aspect of the present invention may have a structure selected from one of the following: hexagonal, cubic, tetragonal, rhombohedral, orthorhombic, monoclinic, triclinic and a combination thereof. For example, the nano-structured material prepared from the method according to any aspect of the present invention may have a lattice structure selected from the group consisting of: hexagonal, cubic, tetragonal, rhombohedral, orthorhombic, monoclinic, triclinic and a combination thereof. In particular, the nano-structured material has a hexagonal lattice structure. Even more in particular, the nano-structured material is hexagonal phase $NaYF_4$, hexagonal phase $NaYF_4$:Yb,Er, hexagonal phase $NaYF_4$:Yb,Tm or hexagonal phase $NaYF_4$:Yb,Ho.

The nano-structured material prepared by the method according to any aspect of the present invention may comprise at least one dimension having size ≦1000 nm. For example, ≦100 nm, in particular, less than 50 nm. In particular, the nano-structured material comprises at least one dimension of size ≦25 nm. Even more in particular, the at least one dimension is of size ≦10 nm.

The nano-structured material prepared by the method according to any aspect of the present invention may be in the form of: nanoparticle(s), nanofilm or monolith. In particular, the at least one nano-structured material may be at least one nanoparticle and the average diameter of the nanoparticle is ≦1000 nm. For example, ≦100 nm, in particular, less than 50 nm. Even more in particular, the average diameter of the nanoparticle is ≦10 nm. The nanoparticle(s) may comprise a core nanoparticle(s) or a core-shell nanoparticle(s).

According to a further aspect, the present invention provides a method of preparing a nano-structured material as described above, wherein the nanoparticle is in the form of a core nanoparticle, and the method further comprises applying at least one organic and/or inorganic material (shell) on the core, to obtain a core-shell nanoparticle(s). According to another further aspect, the present invention provides a method of preparing a nano-structured material as described above, wherein the nanoparticle is in the form of a core nanoparticle, and the nanoparticle further comprises at least one organic and/or inorganic material (shell) applied on the core, to obtain a core-shell nanoparticle(s). The shell may be applied continuously or discontinuously on the core.

The shell of the core-shell nanoparticle may comprise an organic shell material or an inorganic shell material. The shell may comprise a material of the formula $M_1M_2X_t$ or $M_1M_2X_t$:$M_q$, wherein each $M_1$, $M_2$, X, t and $M_q$ are as defined above.

For example, the organic shell material may comprise at least one polymer, a surfactant or a lipid, or a combination thereof. Any suitable polymer, surfactant or lipid may be used for the purposes of the present invention.

The inorganic shell material may comprise $NaM_2F_4$, $LiM_2F_4$, $KM_2F_4$, $RbM_2F_4$, $CsM_2F_4$, $BeM_2F_5$, $Be(M_2)_2F_8$, $MgM_2F_5$, $Mg(M_2)_2F_8$, $CaM_2F_5$, $Ca(M_2)_2F_8$, $SrM_2F_5$, $Sr(M_2)_2F_8$, $BaLnF_5$, $Ba(M_2)_2F_8M_2F_3$, $M_2F_3$, $M_2Cl_3$, $M_2Br_3$, $M_2I_3$, $M_2FClBr$, $M_2OF$, $M_2OCl$, $M_2OBr$, $M_2OS$, $(M_2)_2S_3$, wherein each $M_2$ is the same or different and is selected from the group consisting of: Sc, Y, La, Ce, Pr, Nd, Pm, Sm, Eu, Gd, Tb, Dy, Ho, Er, Tm, Yb and Lu; $SiO_2$; $TiO_2$; ZnS; or a combination thereof.

According to a further aspect, the surface of the nano-structured material may be modified by adding at least one surfactant, lipid, polymer, inorganic material, or a mixture thereof. Any suitable surfactant, lipid, polymer, inorganic material may be used. For example, the surfactant may have Formula (I):

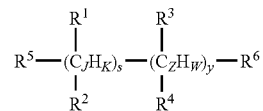

(Formula I)

wherein
each J is the same or different, and 1≦J≦9;
each K is the same or different, and 0≦K≦9;
each s is the same or different, and 0≦s≦9
each Z is the same or different, and 1≦Z≦9;
each W is the same or different, and 0≦W≦9;
each y is the same or different, and 0≦y≦9;
each $R^1$, $R^2$, $R^3$, $R^4$ and $R^5$ is the same or different, and is independently selected from the group consisting of: H, substituted or unsubstituted $C_1$-$C_6$ alkyl, substituted or unsubstituted $C_1$-$C_6$ aryl, HS, COOH, $NH_2$ and OH;
each $R_6$ is the same or different, and is selected from the group consisting of: COOH, $NH_2$, OH, P=0 and P;
with the proviso that s+y<10.

The surfactant may be hydrophilic, hydrophobic and/or amphiphilic.

According to a further aspect, the present invention provides a method of preparing a nano-structured material as described above, wherein a biomolecule is attached to the nano-structured material. The biomolecule may be any suitable biomolecule. For example, the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof.

The present invention also provides a nano-structured material obtainable by the method according to any aspect described above.

According to another aspect, the present invention provides a nano-structured material of formula $M_1M_2X_t$:$M_q$, wherein $M_1$, $M_2$, X, t and $M_q$ are as defined above. The nano-structured material may have a hexagonal lattice structure and may comprise at least one dimension of <50 nm. In particular, the at least one dimension is ≦10 nm.

According to a particular aspect, the present invention provides a nano-structured material of formula $M_1M_2X_t$:$M_q$, wherein $M_1$, $M_2$, X, t and $M_q$ are as defined above, and wherein the nano-structured material has a hexagonal lattice structure, comprising at least one dimension of <50 nm, with the proviso that the nano-structured material is not $LaF_3$:Yb,Er, $LaF_3$:Yb,Ho or $LaF_3$:Yb,Tm. In particular, the at least one dimension is ≦10 nm or ≦5 nm. Even more in particular, the nano-structured material is hexagonal phase $NaYF_4$:$M_q$. For example, $NaYF_4$:$M_q$ is $NaYF_4$:Yb,Er, $NaYF_4$:Yb,Ho or $NaYF_4$:Yb,Tm.

The present invention also provides an article of manufacture comprising any nano-structured material described above. The article of manufacture may be at least one of the following: a display device, a solar cell, an optical data storage, a bio-probe, a carrier for drug delivery, a lamp, a LED, a LCD, a wear resistance, a laser, optical amplifier, and/or a device for bio-imaging.

Another aspect of the present invention is a kit comprising at least one nano-structured material described above and at least one biomolecule. The biomolecule may be any suitable biomolecule. For example, the biomolecule may be selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof.

The present invention also provides a bio-imaging and/or bio-detection system comprising:
- at least one nano-structured material prepared from the method according to any aspect of the invention;
- at least one biomolecule;
- at least one source of excitation; and
- at least one means for delivery of the source of excitation to the system.

The biomolecule may be any suitable biomolecule. For example, the biomolecule may be selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof.

The source of excitation may be any suitable source. For example, the source of excitation is NIR. The NIR may be at 980 nm. The means for delivery of the source of excitation to the system may be any suitable means for delivery. For example, the means for delivery may be optical fibres, endoscopes, external light and/or external laser.

Another aspect of the present invention is a method of modifying at least one hydrophobic structure to make it hydrophilic, comprising applying at least one modifier on the structure surface to make a structure-modifier complex, and wherein the modifier is a surfactant, lipid, polymer and/or inorganic material. The structure may be the nano-structured material as described above. Any suitable surfactant, lipid, polymer and/or inorganic material may be used. The method may comprise applying at least one first modifier on the structure surface, and further a second hydrophilic modifier to make a structure-first modifier-second modifier complex, and wherein the first and/or second modifier is a surfactant, lipid, polymer and/or inorganic material. The method may also comprise applying at least one hydrophilic surfactant on the structure to make a structure-surfactant complex.

BRIEF DESCRIPTION OF THE FIGURES

FIG. 12 (b) shows the TEM picture of (a) at a greater magnification.

FIG. 13 (b) shows the TEM picture of (a) at a greater magnification.

DETAILED DESCRIPTION OF THE INVENTION

Figure 1:
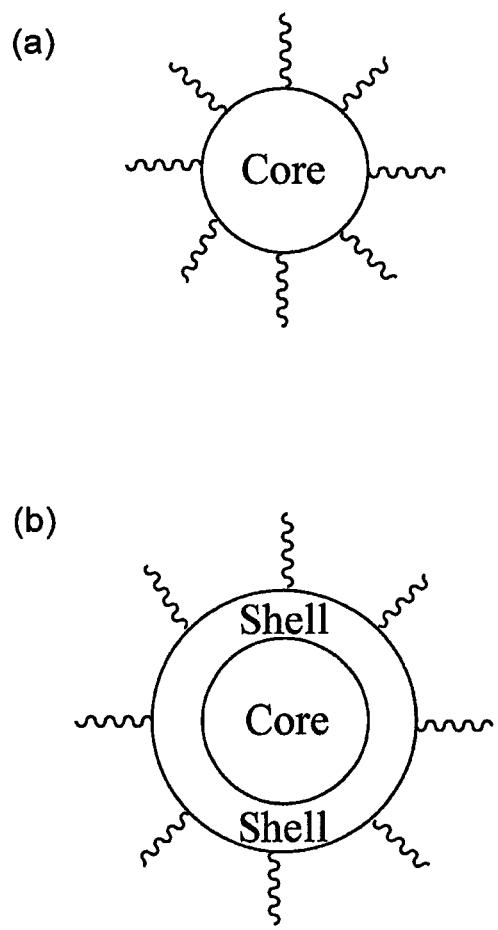
FIG. 1 shows an illustration of (a) core nanoparticles and (b) core/shell nanoparticles and films.

Bibliographic references mentioned in the present specification are for convenience listed in the form of a list of references and added at the end of the examples. The whole content of such bibliographic references is herein incorporated by reference.

The present invention provides a method for preparing nano-structured material of suitable size for use in applications such as bio-imaging and bio-detection. In order to obtain suitable sized nano-structured material, it would be useful to control the crystal structure of the nano-structured material prepared and the size distribution of the nano-structured material. A narrow size distribution would be preferred. For example, the nano-structured material may be used in the bio-imaging and bio-detection of biomolecules.

According to a first aspect, the present invention provides a method of preparing at least one nano-structured material of formula $M_1M_2X_t$ comprising the step of treating (mixing):

at least one compound having the formula $[CX_3(CX_2)_n(CH_2)_mCOO]_pM_1$; and at least one compound having the formula $[CX_3(CX_2)_n(CH_2)_mCOO]_pM_2$;

wherein each X is the same or different and is selected from the group consisting of: halogens, O, S, Se, Te, N, P and As;

$0<t\leq10$;

each n is the same or different and is $0\leq n\leq10$;

each m is the same or different and is $0\leq m\leq10$;

each p is the same or different and is $1\leq p\leq5$;

each $M_1$ is the same or different and is selected from the group consisting of: Li, Na, K, Rb, Cs, Fr, Be, Mg, Ca, Sr, Ba, Ra and $NH_4$;

each $M_2$ is the same or different and is a metal ion.

In particular, the step of treating comprises reacting at least one compound having the formula $[CX_3(CX_2)_n(CH_2)_mCOO]_pM_1$ and at least one compound having the formula $[CX_3(CX_2)_n(CH_2)_mCOO]_pM_2$.

According to a further aspect, the present invention provides a method for preparing at least one nano-structured material of formula $M_1M_2X_t:M_q$ comprising the step of treating (mixing):

at least one compound having the formula $[CX_3(CX_2)_n(CH_2)_mCOO]_pM_1$;

at least one compound having the formula $[CX_3(CX_2)_n(CH_2)_mCOO]_pM_2$; and at least one compound having the formula $[CX_3(CX_2)_n(CH_2)_mCOO]_pM_q$, wherein each $M_q$ is the same or different and is selected from the group consisting of Sc, Y, La, Ce, Pr, Nd, Pm, Sm, Eu, Gd, Tb, Dy, Ho, Er, Tm, Yb and Lu;

t, n, m, p, X, $M_1$ and $M_2$ are as defined above; and each q is the same or different and is $0\leq q\leq10$.

In particular, the step of treating comprises reacting at least one compound having the formula $[CX_3(CX_2)_n(CH_2)_mCOO]_pM_1$; at least one compound having the formula $[CX_3(CX_2)_n(CH_2)_mCOO]_pM_2$ and at least one compound having the formula $[CX_3(CX_2)_n(CH_2)_mCOO]_pM_q$.

The treating in the method according to any aspect of the present invention may be carried out in the presence of at least one source of energy. Accordingly, the method may also be referred to as a method according to any aspect of the invention wherein the method comprises treating the compounds (or the mixing) in the presence of at least one source of energy. For example, the source of energy may be light source, electric source, thermal source, magnetic source, heat source, or a combination thereof. The at least one source of energy may also comprise microwave assisted heating, NIR assisted heating, IR assisted heating, laser heating, X-ray heating. According to a particular aspect, the at least one source of energy is thermal source. The treating may be carried out at a temperature up to 1000° C. In particular, the treating is carried out at a temperature 200° C.-400° C., even more in particular, at a temperature 300° C.-350° C. For example, the treating is carried out at a temperature of 330° C.

According to another aspect, the present invention provides a method of preparing at least one nano-structured material of formula $M_2X_t$ comprising the step of treating (mixing) at least one compound having the formula $[CX_3(CX_2)_n(CH_2)_mCOO]_pM_2$, optionally with at least one compound having the formula $[CX_3(CX_2)_n(CH_2)_mCOO]_pM_q$, in the presence of at least one source of energy, wherein each X is the same or different and is selected from the group consisting of: halogens, O, S, Se, Te, N, P and As;

$0<t\leq10$;

each n is the same or different and is $0\leq n\leq10$;

each m is the same or different and is $0\leq m\leq10$;

each p is the same or different and is $1\leq p\leq5$;

each $M_2$ is the same or different and is a metal ion; and each $M_q$ is as defined as below.

According to another further aspect, the present invention provides a method for preparing at least one nano-structured material of formula $M_2X_t:M_q$ comprising the step of treating (mixing):

at least one compound having the formula $[CX_3(CX_2)_n(CH_2)_mCOO]_pM_2$; and at least one compound having the formula $[CX_3(CX_2)_n(CH_2)_mCOO]_pM_q$, in the presence of at least one source of energy, wherein each $M_q$ is the same or different and is selected from the group consisting of Sc, Y, La, Ce, Pr, Nd, Pm, Sm, Eu, Gd, Tb, Dy, Ho, Er, Tm, Yb and Lu;

t, n, m, p, X, $M_1$ and $M_2$ are as defined above; and each q is the same or different and is $0\leq q\leq10$.

In particular, the step of treating comprises reacting at least one compound having the formula $[CX_3(CX_2)_n(CH_2)_mCOO]_pM_2$ and at least one compound having the formula $[CX_3(CX_2)_n(CH_2)_mCOO]_pM_q$.

Each $M_2$, according to any aspect of the present invention, may be the same or different, and may be any suitable metal ion. For example, each $M_2$ may be the same or different and may be a transition metal ion, inner transition metal ion, or any one of Group I to Group VI metal ion. In particular, each $M_2$ may be selected from the group consisting of: Sc, Y, La, Ce, Pr, Nd, Pm, Sm, Eu, Gd, Tb, Dy, Ho, Er, Tm, Yb and Lu.

According to another aspect, the present invention provides a method which comprises the steps as shown:

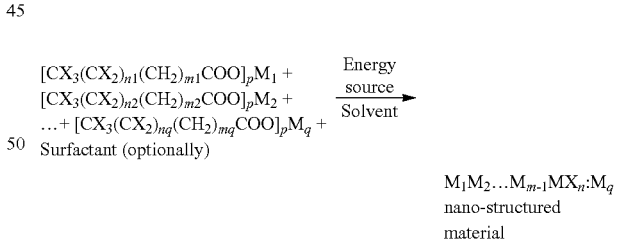

wherein each X may be the same or different and refers to halogen, such as F, Cl, Br and I; each $M_1$ may be the same or different and refers to ions which may be selected from the group consisting of: $NH_4$, Group I and Group II metal ions such as Li, Na, K, Rb, Cs, Be, Mg, Ba, Ca, Sr; $M_2$ to $M_q$ each may be the same or different metal ion and may be selected from the group consisting of rare earth metal ions such as Y, La, Ce Pr, Nd, Sm, Eu, Gd, Tb, Dy, Ho, Er, Tm, Yb, and Lu.

Further, $0<t\leq10$, $0\leq n\leq10$, $0\leq m\leq10$, $1\leq p\leq5$, $0\leq q\leq10$. The surfactant is optional in the method described. Any suitable surfactant, energy source and solvent may be used for the present invention, as will be described below.

According to another aspect, the present invention also provides a method comprising the following reaction:

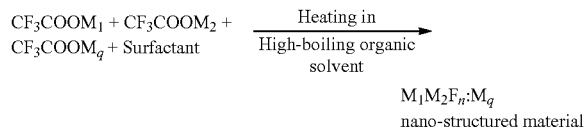

$M_1$, $M_2$, t and $M_q$ may be as described above. For example, each $M_1$ may be the same or different and is selected from the group consisting of: Na, K, Ba, Li and $NH_4$. each $M_2$ may be the same or different and is selected from the group consisting of: Y, La, Gd, Lu. Each $M_q$ may be the same or different and is selected from the group consisting of: Yb, Er, Ho, Tm and a combination thereof, such as Yb—Er, Yb—Ho and Yb—Tm.

$M_q$ according to any aspect of the present invention may act as the dopant. A dopant may be an impurity which is added to a compound in low concentrations to alter some properties of the compound. For example, a dopant may be added in a concentration ranging from one part in a thousand to one part in ten million. It would be understood that a dopant does not alter the crystal structure of the compound it is added to. For example, a dopant may be added to a nano-structured material prepared according to the method of any aspect of the present invention so that the nano-structured material can have additional or enhanced properties. The properties include, but are not limited to, optical properties, magnetic properties, electrical properties and fluorescence.

According to a particular aspect, the nano-structured material prepared according to the method of any aspect of the invention comprising $M_q$ may have fluorescence properties. Fluorescence refers to the emission of light in any wavelength excited with energy source. The energy source may be a light source, electric source, thermal source, magnetic source or a combination thereof. The light source may be at least one of UHV, UV, NIR, visible or X-ray. The light can be of any wavelength. The wavelength of the source may be shorter than the emission. For example, UV excitation with emission in the visible range. The wavelength may be longer than the emission, e.g. NIR excitation with visible emission. The energy source may also be referred to as the excitation source. In particular, the nano-structured materials can be excited with NIR. The NIR may be emitted at visible wavelength. The NIR may be emitted at 980 nm. The excitation source may be a laser source e.g. 980 nm NIR laser.

The compounds used for the method according to any aspect of the present invention may be solid or liquid. The at least one compound of formula $[CX_3(CX_2)_n(CH_2)_m COO]_pM_1$ may be selected from the group consisting of: $CF_3COONa$ and $CF_3COOLi$. The at least one compound of formula $[CX_3(CX_2)_n(CH_2)_m COO]_pM_2$ may be selected from the group consisting of: $(CF_3COO)_3Y$ and $(CF_3COO)_3La$. The at least one compound of formula $[CX_3(CX_2)_n(CH_2)_m COO]_pM_q$ may be selected from the group consisting of: $(CF_3COO)_3Yb$, $(CF_3COO)_3Er$, $(CF_3COO)_3Tm$ and $(CF_3COO)_3Ho$.

In order to achieve suitable nano-structured material prepared according to the method of any aspect of the invention, it may be useful to control the parameters involved in the preparation of the nano-structured material. For example, the condition(s) at which the treating step of the method is carried out may affect the nano-structured material prepared by the method. The conditions may include the source of energy and/or any solvent used in the method according to any aspect of the present invention.

For the purposes of the present invention, a nano-structured material is defined as being one comprising constituents which has at least one dimension in the nanoscale.

The nano-structured material prepared from the method according to any aspect of the present invention may comprise at least one dimension having size $\leq 1000$ nm. For example, $\leq 100$ nm, in particular, $\leq 50$ nm and even more in particular, less than 50 nm. More in particular, the nano-structured material may comprise at least one dimension of sizes $\leq 25$ nm, and even more in particular the nano-structured material may comprise at least one dimension of size $\leq 10$ nm or $\leq 5$ nm. According to a particular aspect, the nano-structured material prepared according to any method of the invention, may comprise one, two, three, four, five, six or even more dimension(s), each dimension of size $\leq 1000$ nm, $\leq 100$ nm, $\leq 50$ nm, less than 50 nm, $\leq 25$ nm, $\leq 10$ nm or $\leq 5$ nm. According to a more particular aspect, the nano-structured material prepared according to method of the invention, may comprise one, two, three, four, five, six or even more dimension(s), each dimension of size less than 50 nm, $\leq 25$ nm, $\leq 10$ nm or $\leq 5$ nm. The dimension may refer to the average diameter of the nano-structured material.

The treating in the method according to any aspect of the present invention may be carried out in the presence of at least one source of energy. Accordingly, the method may also be referred to as a method according to any aspect of the invention wherein the method comprises treating the compounds in the presence of at least one source of energy. For example, the source of energy may be light source, electric source, thermal source, magnetic source, heat source, or a combination thereof. The at least one source of energy may also comprise microwave assisted heating, NIR assisted heating, IR assisted heating, laser heating, X-ray heating. According to a particular aspect, the at least one source of energy is thermal source. The treating may be carried out at a temperature up to 1000° C. In particular, the treating is carried out at a temperature 200° C.-400° C., even more in particular, at a temperature 300° C.-350° C. For example, the treating is carried out at a temperature of 330° C.

The treating in the method according to any aspect of the present invention may be carried out in the presence of at least one solvent. Solvent may be defined as being a fluid phase (such as liquid, gas or plasma) that dissolves a solid, liquid or gaseous compound, resulting in a solution. The at least one solvent may be a polar solvent, a non-polar solvent, or a mixture thereof. Any suitable polar solvent and non-polar solvent may be used for the present invention.

For example, the polar solvent may be selected from the group consisting of: water, methanol, ethanol, propyl alcohol, butanol, pentanol, hexanol, ketone, ethylene glycol, glycerol, propylene glycol, polyethylene glycol, ethyl acetate, esters and a combination thereof.

The non-polar solvent may be selected from the group consisting of: oleylamine, octadecene, oleic acid, alkyl amine, dialkyl amine, trialkyl amine, alkenyl amine, dialkenyl amine, trialkenyl amine, alkyl acid, alkenyl acid, trialkyl phosphine, trialkyl phosphine oxide, trialkylphosphate, alkane, alkene, alkyl ether, alkenyl ether and a combination thereof.

The at least one solvent may be an organic solvent, inorganic solvent or a mixture thereof. Examples of organic solvent include solvents which contain carbon atom(s), such as acetone, alcohol, benzene, benzol, carbon disulphide, carbon tetrachloride, chloroform, ether, ethyl acetate, furfural, gasoline, toluene, turpentine, xylene, xylol, octadecane, tetracosane, oleylamine or oleic acid. Inorganic solvents are solvents which do not contain carbon atom(s), such as water.

The nano-structured material prepared from the method according to any aspect of the present invention may be selected from the group consisting of: $NaM_2F_4$, $LiM_2F_4$, $KM_2F_4$, $RbM_2F_4$, $CsM_2F_4$, $BeM_2F_5$, $Be(M_2)_2F_8$, $MgM_2F_5$, $Mg(M_2)_2F_8$, $CaM_2F_5$, $Ca(M_2)_2F_8$, $SrM_2F_5$, $Sr(M_2)_2F_8$, $BaLnF_5$, $Ba(M_2)_2F_8M_2F_3$, $M_2F_3$, $M_2Cl_3$, $M_2Br_3$, $M_2I_3$, $M_2FClBr$, $M_2OF$, $M_2OCl$, $M_2OBr$, $M_2OS$ and $(M_2)_2S_3$. $M_2$ may be as defined above. In particular, each $M_2$ is the same or different and is selected from the group consisting of: Sc, Y, La, Ce, Pr, Nd, Pm, Sm, Eu, Gd, Tb, Dy, Ho, Er, Tm, Yb and Lu. In particular, the nano-structured material is $NaYF_4$, $LiYF_4$, $BaYF_4$, $NaLaF_4$, $LaF_3$, $YF_3$, $CeF_3$, $GdF_3$ or YOF. Even more in particular, the nano-structured material is $NaYF_4$.

According to a particular aspect, the nano-structured material prepared from the method according to any aspect of the present invention may be selected from the group consisting of: $NaM_2F_4:M_q$, $LiM_2F_4:M_q$, $KM_2F_4:M_q$, $RbM_2F_4:M_q$, $CsM_2F_4:M_q$, $BeM_2F_5:M_q$, $Be(M_2)_2F_8:M_q$, $MgM_2F_5:M_q$, $Mg(M_2)_2F_8:M_q$, $CaM_2F_5:M_q$, $Ca(M_2)_2F_8:M_q$, $SrM_2F_5:M_q$, $Sr(M_2)_2F_8:M_q$, $BaM_2F_5:M_q$, $Ba(M_2)_2F_8:M_q$, $M_2F_3:M_q$, $M_2Cl_3:M_q$, $M_2Br_3:M_q$, $M_2I_3:M_q$, $M_2FClBr:M_q$, $M_2OF:M_q$, $M_2OCl:M_q$, $M_2OBr:M_q$, $M_2OS:M_q$, $(M_2)_2S_3:M_q$, wherein each $M_2$ and each $M_q$ are as defined above. In particular, each $M_2$ is the same or different and is selected from the group consisting of: Sc, Y, La, Ce, Pr, Nd, Pm, Sm, Eu, Gd, Tb, Dy, Ho, Er, Tm, Yb and Lu, and each $M_q$ is the same or different and is selected from the group consisting of: Yb, Er, Tm and Ho. In particular, the nano-structured material is $NaYF_4$:Yb, Er, $NaYF_4$:Yb,Tm, $NaYF_4$:Yb,Ho, $LiYF_4$:Yb,Er, $BaYF_5$:Yb,Er, $NaLaF_4$:Yb,Er, $LaF_3$:Yb,Er, $CeF_3$:Yb,Er, $GdF_3$:Yb,Er, $YF_3$:Yb,Er, YOF:Yb,Er, $LaF_3$:Yb,Tm, $CeF_3$:Yb,Tm, $GdF_3$:Yb,Tm, $YF_3$:Yb,Tm or YOF:Yb,Tm. Even more in particular, the nano-structured material is $NaYF_4$:Yb,Er, $NaYF_4$:Yb,Tm or $NaYF_4$:Yb,Ho.

The nano-structured material prepared from the method according to any aspect of the present invention may have a structure selected from the group consisting of: hexagonal, cubic, tetragonal, rhombohedral, orthorhombic, monoclinic, triclinic and a combination thereof. In particular, the nano-structured material prepared from the method according to any aspect of the present invention may have a lattice structure selected from the group consisting of: hexagonal, cubic, tetragonal, rhombohedral, orthorhombic, monoclinic, triclinic and a combination thereof. It will be understood that for the purposes of the present invention, the lattice structure of nano-structured material describes the grouping of the material according to the axial system. Each lattice structure consists of a set of three axes in a particular geometrical arrangement. The nano-structured material's lattice structure may play a role in determining some of its properties, such as its electric properties and optical properties.

In particular, the nano-structured material has a hexagonal lattice structure. For example, the nano-structured material may be hexagonal phase $NaYF_4$. Even more in particular, the nano-structured material is hexagonal phase $NaYF_4$:Yb,Er, hexagonal phase $NaYF_4$:Yb,Tm or hexagonal phase $NaYF_4$:Yb,Ho.

The nano-structured material prepared from the method according to any aspect of the present invention may be in the form of: nanoparticle(s), nanofilm, or monolith. For example, the nano-structured material may be at least one nanoparticle and the average diameter of the nanoparticle(s) is $\leq 1000$ nm, $\leq 100$ nm, $\leq 50$ nm, $<50$ nm, $\leq 25$ nm, $\leq 10$ nm or $\leq 5$ nm. In particular, the average diameter of the nanoparticle(s) is $<50$ nm, $\leq 25$ nm, $\leq 10$ nm or $\leq 5$ nm. More in particular, the average diameter of the nanoparticle(s) is $\leq 10$ nm.

The nano-structured material may be at least one nanofilm. The nanofilm may have a thickness between 0.1 nm to 1 mm. In particular, the nanofilm thickness may be the same or less than 500 nm, 400 nm, 300 nm, 200 nm, 100 nm, 50 nm, 25 nm, 20 nm, 15 nm, 10 nm or 5 nm. The nanofilm may be a single layer or multiple layers, and wherein each layer of the nanofilm is the same or different from the other layer. The nanofilms may be prepared by depositing particles using methods such as dip coating or spin coating.

Figure 2:
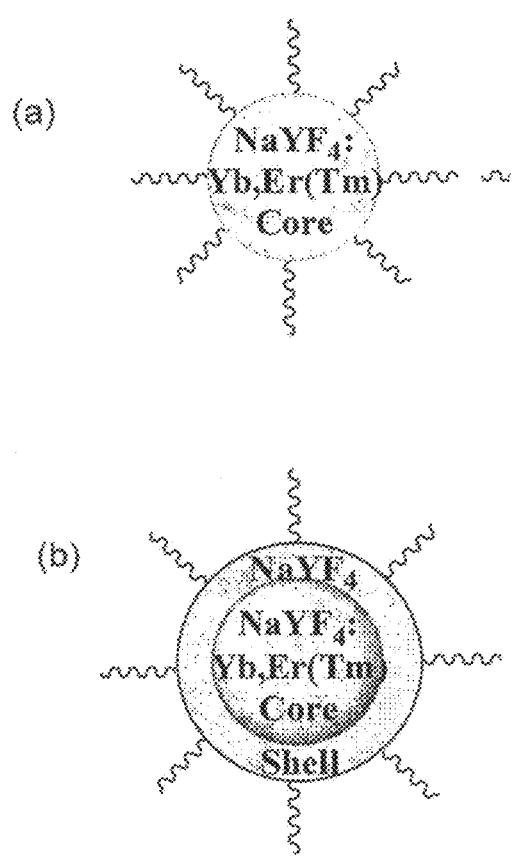
FIG. 2 shows an illustration of (a) the core and (b) core/shell structured $NaYF_4$:Yb,Er(Tm)/$NaYF_4$ nanoparticles.

The nanoparticle(s) may comprise core nanoparticle(s) and/or core-shell nanoparticle(s). The shell may be the same or different material as the core. An illustration of the core nanoparticle and core-shell nanoparticle is shown in FIGS. 1(a) and 1(b) respectively FIG. 1(a) shows a core nanoparticle with at least one kind of surfactant on its surface. FIG. 1(b) shows a core-shell nanoparticle with at least one kind of surfactant on the shell. FIG. 2 shows a nano-structured material where the core and the shell are of the same material, $NaYF_4$. For example, the nanoparticle may be a core nanoparticle and the nanoparticle further comprises at least one organic and/or inorganic material (shell) applied on the core, to obtain a core-shell nanoparticle(s). Accordingly, the method according to any aspect of the present invention may comprise a further step of applying at least one organic and/or inorganic material (shell) on the core to obtain a core-shell nanoparticle(s).

As mentioned above, the nanoparticle may comprise an organic and/or inorganic material (shell). The organic and/or inorganic material (shell) may be applied continuously or discontinuously on the core. According to a particular aspect, the shell material has the formula $M_1M_2X_t$ or $M_1M_2X_t:M_q$, wherein $M_1$, $M_2$, X, t and $M_q$ are as defined above. For example, the shell material may comprise a material selected from the group consisting of: $NaM_2F_4$, $LiM_2F_4$, $KM_2F_4$, $RbM_2F_4$, $CsM_2F_4$, $BeM_2F_5$, $Be(M_2)_2F_8$, $MgM_2F_5$, $Mg(M_2)_2F_8$, $CaM_2F_5$, $Ca(M_2)_2F_8$, $SrM_2F_5$, $Sr(M_2)_2F_8$, $BaLnF_5$, $Ba(M_2)_2F_8M_2F_3$, $M_2F_3$, $M_2Cl_3$, $M_2Br_3$, $M_2I_3$, $M_2FClBr$, $M_2OF$, $M_2OCl$, $M_2OBr$, $M_2OS$, $(M_2)_2S_3$, wherein $M_2$ is as defined above. In particular, each $M_2$ is the same or different and is selected from the group consisting of: Sc, Y, La, Ce, Pr, Nd, Pm, Sm, Eu, Gd, Tb, Dy, Ho, Er, Tm, Yb and Lu.

According to another particular aspect, the organic shell material may comprise at least one polymer, a surfactant, a lipid, or a combination thereof. For example, the polymer may be selected from the group consisting of: polystyrene (PS), polyethylene (PE), polymethyl methacrylate (PMMA), polylactic acid (PLA) and a combination thereof. For the purposes of the present invention, a surfactant will be understood to be on which is a surface active agent that lowers the surface tension. The surfactant may contain both hydrophilic and hydrophobic components and may be semi-soluble in both organic and aqueous solvents. For example, surfactants tend to clump up when in solution, forming a surface between fluid and air with hydrophobic tails in the air and the hydrophilic heads in the fluid.

The inorganic shell material may comprise any one of the following: $NaM_2F_4$, $LiM_2F_4$, $KM_2F_4$, $RbM_2F_4$, $CsM_2F_4$, $BeM_2F_5$, $Be(M_2)_2F_8$, $MgM_2F_5$, $Mg(M_2)_2F_8$, $CaM_2F_5$, $Ca(M_2)_2F_8$, $SrM_2F_5$, $Sr(M_2)_2F_8$, $BaLnF_5$, $Ba(M_2)_2F_8M_2F_3$, $M_2F_3$, $M_2Cl_3$, $M_2Br_3$, $M_2I_3$, $M_2FClBr$, $M_2OF$, $M_2OCl$, $M_2OBr$, $M_2OS$, $(M_2)_2S_3$, wherein each $M_2$ is the same or different and is selected from the group consisting of: Sc, Y, La, Ce, Pr, Nd, Pm, Sm, Eu, Gd, Tb, Dy, Ho, Er, Tm, Yb and Lu; $SiO_2$; $TiO_2$; ZnS; or a combination thereof.

The shell material may confer certain properties onto the nano-structured material. For example, the shell may make the nano-structured material more hydrophilic, hydrophilic or amphiphilic. In particular, the nano-structured material may be made hydrophilic in order to better attach the nano-structured materials to biomolecules such as proteins and DNA.

According to a further aspect, the nano-structured material prepared from the method according to any aspect of the present invention may have its surface modified. The surface of the nano-structured material may be modified by adding at least one surfactant, lipid, polymer, inorganic material, or a mixture thereof. The surface of the nano-structured material may be modified to confer certain properties onto the nano-structured material. For example, the surface of the nano-structured material may be modified to make the nano-structured material more hydrophilic, hydrophilic or amphiphilic. In particular, the nano-structured material may be made hydrophilic in order to better attach the nano-structured materials to biomolecules such as proteins and DNA. The nano-structured material may be made more hydrophilic by surfactant(s) and/or lipid(s).

According to a particular aspect, the nano-structured material may be surface modified by any one of the following ways:

(a) Surfactant/lipids modification:

Nano-structured material+surfactant(s)→nano-structured material-Surfactants complex (b) Surfactant(s)/lipid(s) replacement:

Nano-structured material-Surfactant(1)+Surfactant (2)→Nano-structured material-surfactant(2)

(c) Surfactant attached on the surfactant on the nano-structure material surface Nanoparticles-Surfactant(1)+Surfactant (2)→Nano-structured material-Surfactant(1)-Surfactant(2)

Figure 3:
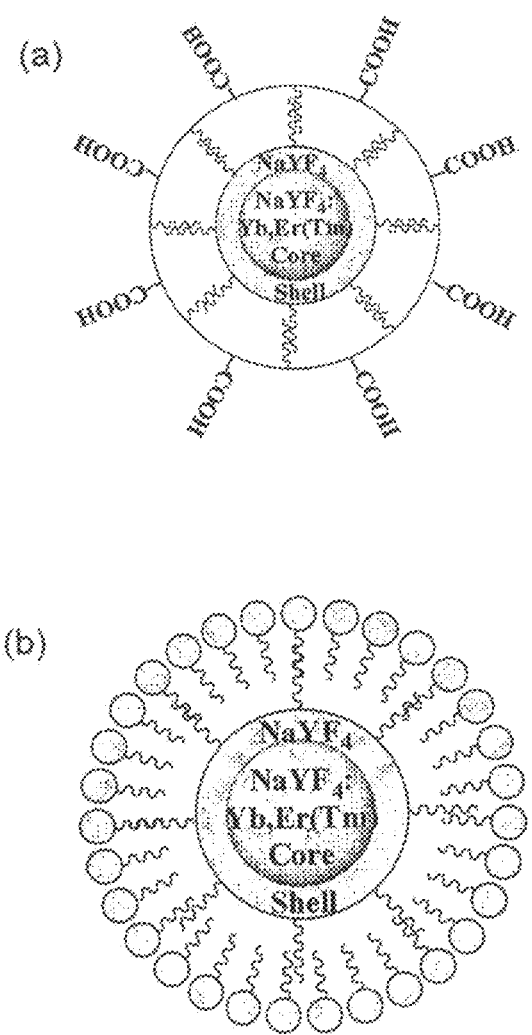
FIG. 3 shows an illustration of (a) poly acrylic acid (PAA) caped $NaYF_4$:Yb,Er(Tm)/$NaYF_4$ nanoparticles and (b) PEG-phospholipids caped $NaYF_4$:Yb,Er(Tm)/$NaYF_4$ nanoparticles.

It will be understood that in the above, surfactant and lipid may be used interchangeably. An illustration of surface modified nano-structured material is shown in FIG. 3.

Figure 4:
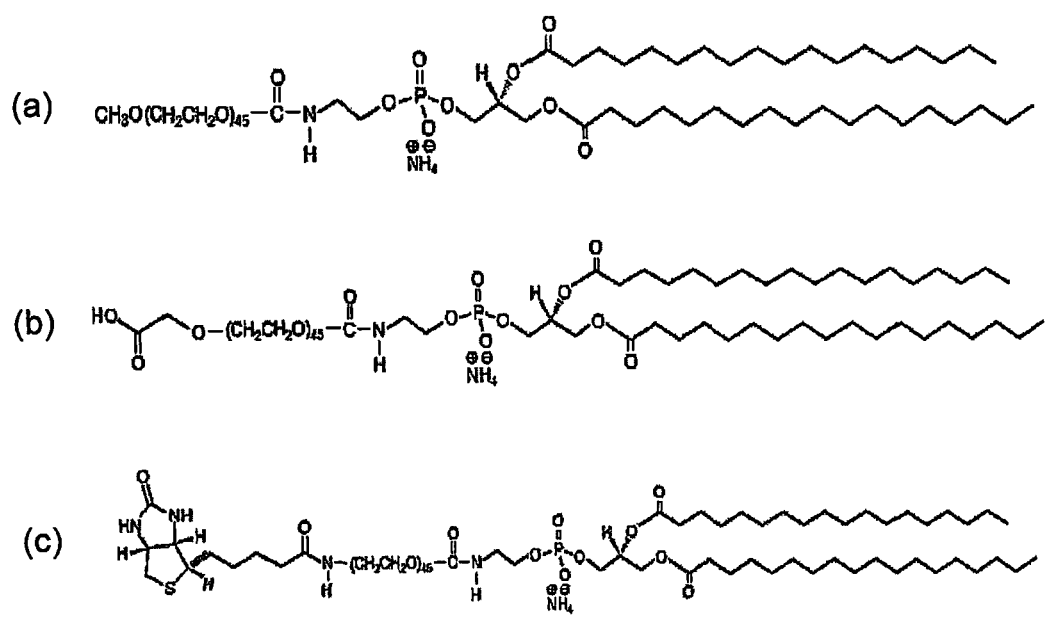
FIG. 4 shows the structure of three examples of lipids: (a) 18:0 mPEG2000PE, (b) DSPE-PEG(2000) carboxylic acid and (c) DSPE-PEG(2000) Biotin.

The surface of the nano-structured material may be modified by at least one lipid. The lipid may be any suitable lipid. For example, the lipid may be phospholipid, long-chain aliphatic hydrocarbon, lipid multichain, comb-shaped lipid-polymer steroid, fullerene, polyaminoacid, native or denatured protein, aromatic hydrocarbon, or partially or completely fluorinated lipid. In particular, the lipid may have the structure as shown in FIGS. 4 (a), (b) and (c).

In particular, the surface is modified by at least one surfactant. The at least one surfactant may be adsorbed onto the surface of the nano-structured material. The surfactant according to any aspect of the present invention may be hydrophilic, hydrophobic and/or amphiphilic. The surfactant may have the following formula:

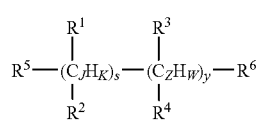

(Formula I)

wherein
each J is the same or different, and $1 \leq J \leq 9$;
each K is the same or different, and $0 \leq K \leq 9$;
each s is the same or different, and $0 \leq s \leq 9$;
each Z is the same or different, and $1 \leq Z \leq 9$;
each W is the same or different, and $0 \leq W \leq 9$;
each y is the same or different, and $0 \leq y \leq 9$;
each $R^1$, $R^2$, $R^3$, $R^4$ and $R^5$ is the same or different, and is independently selected from the group consisting of: H, substituted or unsubstituted $C_1$-$C_6$ alkyl, substituted or unsubstituted $C_1$-$C_6$ aryl, HS, COOH, $NH_2$ and OH;
each $R_6$ is the same or different, and is selected from the group consisting of: COOH, $NH_2$, OH, P=O and P;
with the proviso that $s+y<10$.

As used herein, the term "alkyl" refers to a straight or branched, monovalent, saturated aliphatic chain of preferably 1 to 6 carbon atoms, including normal, iso, neo and tertiary. "Alkyl" includes, but is not limited to, methyl, ethyl, propyl, isopropyl, butyl, iso-butyl, sec butyl, tert butyl, amyl, isoamyl, neoamyl, hexyl, isohexyl, neohexyl, and the like; cycloalkyl group such as cyclopropyl, cyclobutyl, cyclopentyl, cyclohexyl and the like, the cycloalkyl group may be substituted. The alkyl may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or $S(O)_2$, P, P(O), $P(O)_2$ atoms.

The term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, biphenyl, naphthyl, furanyl, pyrrolyl, thiophenyl, pyridinyl, indolyl, benzofuranyl, benzothiophenyl, quinolinyl, isoquinolinyl, imidazolyl, thiazolyl, pyrazinyl, pyrimidinyl, purinyl and pteridinyl and the like.

The term "lower" refers to a group having between one to six carbon atoms.

Any suitable surfactant as described in the Sigma Aldrich catalogue, 2004-2005 may be used for the present invention. In particular, the surfactant used may be at least one or a mixture of the following:

(i) a surfactant, comprising thiol and carboxylic acid functional groups, selected from mercaptosuccinic acid, mercaptobenzoic acid, penicillamine, mercaptopropioinyl glycine, thioldiacetic acid, thiodipropionic acid, and cysteine hydrochloride;

(ii) a surfactant, comprising thiol and amine functional groups, selected from cysteine, mercaptoethylamine, thioguanine, and thioacetamide;

(iii) a surfactant, comprising thiol and hydroxyl groups, selected from mercaptoethanol, thiodiethanol, thioglucose, thioglycerol and cysteine-OH;

(iv) cysteine; and/or (v) a peptide comprising cysteine.

For example, in the surfactant(s) of Formula (I), s+y has the following ranges: 1-9, 1-8, 1-7, 1-6, 1-5, 1-4, 1-3, 1-2, or 1. In particular, s+y is 1-4, preferably 1 or 2, and each of $R^1$, $R^2$, $R^3$, and $R^4$, independently, is not present or is H. More in particular, surfactant(s) according to any aspect of the present invention may be $HSCH_2COOH$ and/or $HS(CH_2)_2COOH$. The cysteine-containing peptide of (v) may be a peptide of the following sequence: CDPGYIGSR (SEQ ID NO:1). SEQ ID NO:1 refers to the 925-933 laminin fragment. In particular, the surfactant is polyacrylic acid, polyethylene glycol 600 (HOOC-PEG-COOH), 11-aminoundecanoic acid (AUA) or a mixture thereof.

According to a further aspect, a biomolecule may be attached to the nano-structured material prepared from the method according to any aspect of the present invention. Therefore, the method according to any aspect of the present invention may comprise a further step of attaching a biomolecule to the nano-structured material. The biomolecule may be attached to the nano-structured material by chemical or physical conjugation. Any suitable biomolecule may be attached to the nano-structured material. For example, the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof. In particular, the biomolecule is streptavidin, an antibody, DNA or a combination thereof. Other biomolecules with free amine, hydroxyl or carboxyl groups which could be attached to surfactants as described above include anti-cancer drugs such as carboplatin, nedaplatin, JM216, methotrexate and doxorubicin, as well as proteins and glycoproteins such as herceptin.

According to another aspect, the present invention provides a nano-structured material obtainable by any method described above. The nano-structured material may further comprise at least one surfactant, lipid and/or polymer. A suitable biomolecule, as described above, may be attached to the nano-structured material.

The nano-structured material according to any aspect of the present invention may provide a fluorescent dye that can be embedded or mixed or coated with another semiconductor matrix for the generation of electrical current. For example, the absorption of NIR, visible or UV light to generate electrical current in a dye-sensitized solar cell.

According to yet another aspect, the present invention provides a nano-structured material of formula $M_1M_2X_t$:$M_q$, wherein each of $M_1$, $M_2$, $M_q$, X and t are as defined above, and wherein the nano-structured material has a hexagonal (lattice) structure and comprises at least one dimension of size $\leq$1000 nm, $\leq$100 nm, $\leq$50 nm, <50 nm, $\leq$25 nm, $\leq$10 nm or $\leq$5 nm. In particular, the nano-structured material comprises at least one dimension of $\leq$10 nm.

In particular, the present invention provides a nano-structured material of formula $M_1M_2X_t$:$M_q$, wherein $M_1$, $M_2$, X, t and $M_q$ are as defined above, and wherein the nano-structured material has a hexagonal lattice structure, comprising at least one dimension of <50 nm, with the proviso that the nano-structured material is not $LaF_3$:Yb,Er, $LaF_3$:Yb,Ho or $LaF_3$:Yb,Tm. Even more in particular, the nano-structured material is hexagonal phase $NaYF_4$:$M_q$. For example, $NaYF_4$:$M_q$ is $NaYF_4$:Yb,Er, $NaYF_4$:Yb,Ho or $NaYF_4$:Yb,Tm. The nano-structured material may have a hexagonal (lattice) structure and comprise at least one dimension of size $\leq$1000 nm, $\leq$100 nm, $\leq$50 nm, <50 nm, $\leq$25 nm, $\leq$10 nm or $\leq$5 nm. In particular, the nano-structured material comprises at least one dimension of $\leq$10 nm.

The present invention also provides an article of manufacture comprising the any nano-structured material as described above. For example, the article of manufacture may be at least one of the following: a display device, a solar cell, an optical data storage, a bio-probe, a carrier for drug delivery, a lamp, a LED, a LCD, a wear resistance, a laser, optical amplifier, low density IR imaging, mercury-free fluorescent lamps, plasma display panel (PDP) and/or a device for bio-imaging. For example, nano-structured material such as $BaYF_5$, $BaY_2F_8$, $LiYF_4$, $NaM_2F_4$ and $M_2F_3$, wherein each $M_2$ is the same or different and is as described above, are efficient hosts for near-infrared emission ions such as $Nd^{3+}$, $Er^{3+}$, $Ho^{3+}$ and $Pr^{3+}$. Because the emissions fall in the telecommunication windows, the nano-structured materials can be used as optical amplifiers in telecommunication.

$BaYF_5$, $BaY_2F_8$, $LiYF_4$, $NaM_2F_4$ and $M_2F_3$, wherein each $M_2$ is the same or different and is as defined above, are also the efficient hosts for quantum cutting phosphors, which can absorb a high energy VUV photon, giving off two or more visible photons. The total quantum efficiency is therefore more than 100%. Such nano-structured materials have applications which include mercury-free fluorescent lamp and plasma display panel (PDP).

Oil dispersible $BaYF_5$, $BaY_2F_8$, $LiYF_4$, $NaM_2F_4$ and $M_2F_3$, wherein each $M_2$ is the same or different and is as defined above, are nano-structured materials which are antiwear and may be used as extreme pressure additives due to their tribological and lubricating behaviour.

According to another aspect, the present invention provides a kit comprising at least one nano-structured material as described above and at least one biomolecule. The biomolecule may be any suitable biomolecule. For example, the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide, and a mixture thereof. In particular, the biomolecule is streptavidin, an antibody, DNA or a combination thereof. The kit may further comprise at least one surfactant as described above. The kit may also comprise a suitable excitation source and/or means for delivery of the excitation source as described herein. In particular, the excitation source is NIR. More in particular, the excitation source is NIR laser at 980 nm. The means for delivery of the excitation source may be optical fibres or endoscopes. The kit may be used in bio-imaging and/or bio-detection. For example, the kit may be used for labelling a tissue sample. When the tissue is labelled with the nano-structured material of the present invention, and a source of excitation is provided, the tissue which is affected by cancer, for example, will emit fluorescence, indicating the presence of cancer.

Another aspect of the present invention is a bio-imaging and/or bio-detection system comprising:
 at least one nano-structured material prepared from the method described above;
 at least one biomolecule;
 at least one source of excitation; and
 at least one means for delivery of the source of excitation to the system.

For example, the system may be used for detecting cancer. In particular, a tissue sample is labelled with the nano-structured material of the present invention. When a source of excitation is provided, the tissue which is affected by cancer, for example, will emit fluorescence, indicating the presence of cancer. The system may also be used in the detection of specific viruses or biomolecules in blood, for example, by detecting the fluorescence of the nano-structured material when a source of excitation is provided.

The biomolecule may be any suitable biomolecule. For example, the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof. In particular, the biomolecule is streptavidin, an antibody, DNA or a combination thereof.

The source of excitation may be any suitable source. For example, the source of excitation may be a microwave source, NIR source, IR source, laser source, X-ray source or a combination thereof. In particular, the source may be NIR source. In particular, the NIR source is at 980 nm.

Any suitable means for delivery of the source of excitation to the system may be used. For example, the means for delivery may be selected from the group consisting of: optical fibres, endoscopes, external light, external laser and a combination thereof. The optical fibres may be inserted in a needle. The source of excitation may also be delivered through the skin surface.

The present invention also provides a nano-structured material prepared according to a method as described above for use as fluorescent sensors for bio-imaging and/or detection of biomolecule(s). For example, the nano-structured material prepared may be used for labelling cells or tissues and to observe the image via a fluorescent microscopy. The nano-structured material may also be used for labelling biomolecules such as proteins and detecting the fluorescent signal.

The present invention also provides a method of modifying the surface of a nano-structured material to alter, change or modify its properties. For example, the surface modification may be carried out by adding at least one surfactant, lipid, polymer, inorganic material, or a mixture thereof. The nano-structured material may be the nano-structured material as described above or any other nano-structured material. This surface modification may also be applied to any compound, molecule, structure or material. The surface modification may be as described above. For example, the surface modification may be used for making a hydrophobic material hydrophilic. The present invention also provides a method of modifying at least one hydrophobic structure to make it hydrophilic, comprising applying at least one modifier on the structure surface to make a structure-modifier complex, and wherein the modifier is a surfactant, lipid, polymer and/or inorganic material. The structure may be the nano-structured material as described above. For example, the method may comprise applying at least one first modifier on the structure surface, and further a second hydrophilic modifier to make a structure-first modifier-second modifier complex, wherein the first and/or second modifier is a surfactant, lipid, polymer and/or inorganic material. Any suitable surfactant, lipid, polymer and/or inorganic material may be used. For example, the surfactants, lipids, polymers and/or inorganic material described above may be used as the first and/or second modifier. According to a particular aspect, the method may comprise applying at least one hydrophilic surfactant on the structure to make a structure-surfactant complex.

The present invention also provides a method of varying the length of the at least one surfactant(s) on the nano-structured material so as to modulate the efficiency of loading of the biomolecule(s) on the surfactant(s), as well as to modulate the NIR optical properties of the NIR-sensitive nano-structured material. In particular, the modulation is obtained by varying the chain length of the at least one surfactant and determining the improved efficiency of loading biomolecule(s) on the surface modified nano-structured material, and/or improved efficiency of releasing biomolecule(s) from the surface modified nano-structured material following light irradiation.

The surface modification of the nano-structured material with surfactants facilitates the binding of functional molecules, such as biomolecules. Suitable surfactants have functional groups reactive to both the nano-structured material and desired biomolecules. The inorganic-organic surface interactions between the surfactants and the nano-structured material may be used to modulate (manipulate) the optical properties of the biomolecule delivery system in which the nano-structured material is used. For the same number of functional groups on each surfactant, the reactivity and number of binding sites may be modified by altering the surfactant intermolecular and surfactant-particle interactions through differences in the surfactant chain length. The alteration of surfactant interactions to control the binding intensity would be applicable to systems surface functionalised with biomolecules.

Accordingly, the present invention provides a method of modulating the biomolecule loading efficiency on the nano-structured material which has been surface modified by at least one surfactant according to any embodiment of the invention, comprising varying the chain length of the at least one surfactant adsorbed on the nano-structured material.

In particular, the surfactant is at least one surfactant or a mixture thereof of the surfactant of Formula (I).

In particular, the method is a method for increasing the biomolecule loading efficiency comprising varying the chain length of the at least one surfactant as described above, so that the biomolecule loading efficiency is higher (increased). Even more in particular, the surfactant is at least one surfactant or a mixture thereof of the surfactant of Formula (I).

Further, the present invention provides a method of modulating binding affinity and/or binding recognition of the surface modified nano-structured material ligand(s) (sensors) with the respective receptor(s). The nano-structured material may be surface modified having at least one surfactant adsorbed onto the surface of the nano-structured material. The modulation of the binding affinity and/or binding recognition of particular kind of biomolecule(s), that is, ligand(s) (sensors) loaded on the surface modified nano-structured material according to any embodiment of the invention can be carried out, for example, by altering the surfactant interaction.

The nano-structured material as described above may be used as bio-probes. Accordingly, the expensive Ti-Sa laser system may be replaced with a cheaper 980 nm semiconductor laser system instead. The price of a multi-photon microscope may be comparable or even lower than that of the traditional confocal microscope.

Having now generally described the invention, the same will be more readily understood through reference to the following examples which are provided by way of illustration, and are not intended to be limiting of the present invention.

EXAMPLES

Characterisation Techniques

TEM images of the nano-structured materials were collected on a JEOL JEM 3010 transmission electron microscope. Powder X-ray diffraction spectra were acquired with a D8 advance x-ray diffractometer, with Cu Kα radiation at 1.5406 Å. Size distribution and zeta-potentials of the nano-structured materials were determined using a dynamic light scattering instrument (Nano-ZS, Malvern Instruments). Up-conversion fluorescence spectra were obtained on a LS-55 luminescence spectrometer (Perkin-Elmer) with an external 980 nm laser diode (1 W, continuous wave with 1 m fibre, Beijing Viasho Technology Co.) as the excitation source in place of the xenon lamp in the spectrometer. The spectrometer operated at the bioluminescence mode, with gate time 1 ms, delay time 1 ms, cycle 20 ms and flash count 1. For comparison, colloidal solutions of core, core-shell in chloroform, and core-shell-polymer in water with the same concentration were used.

Example 1

Synthesis of Nanoparticles (Core or Core/Shell Structure)

Example 1.1

Synthesis of Hexagonal Phase $NaYF_4$:Yb,Er and $NaYF_4$:Yb,Tm Nanoparticles

For the synthesis of hexagonal $NaYF_4$:20% Yb,2% Er and $NaYF_4$:20% Yb,2% Tm nanoparticles, a mixture of 2 mmol $CF_3COONa$, 0.78 mmol of $(CF_3COO)_3Y$, 0.2 mmol of $(CF_3COO)_3Yb$ and 0.02 mmol of $(CF_3COO)_3Er/(CF_3COO)_3Tm$ was dissolved in 10 ml of oleylamine, and then passed through a 0.22 μm filter (Millipore) to remove any residue. Under vigorous stirring in a 50 ml flask, the mixture was heated to 330° C. in the presence of argon for protection from oxidation. After 1 h, heating was stopped. The transparent yellowish reaction mixture obtained was allowed to cool to 80° C. before 20 ml of ethanol was added to the mixture. The nanoparticles were isolated by centrifuging. They were washed 3 times with hexane and 3 times with de-ionized water to remove any NaF residue. The scheme of the reaction was as follows:

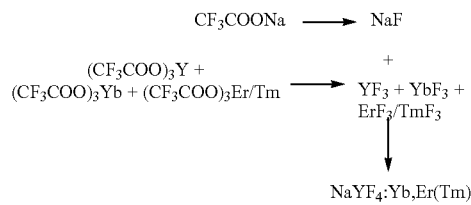

Figure 5:
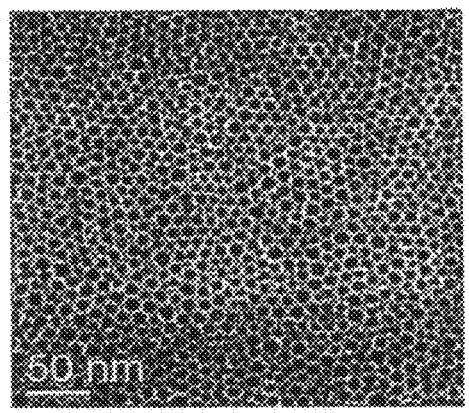
FIG. 5 shows the TEM pictures of the hexagonal phase $NaYF_4$:Yb,Er and $NaYF_4$:Yb,Tm nanoparticles at a magnification of (a) 50K (b) 150K and, (c) XRD pattern and (d) SAED pattern of the hexagonal phase $NaYF_4$:Yb,Er and $NaYF_4$:Yb,Tm nanoparticles.
Figure 5:
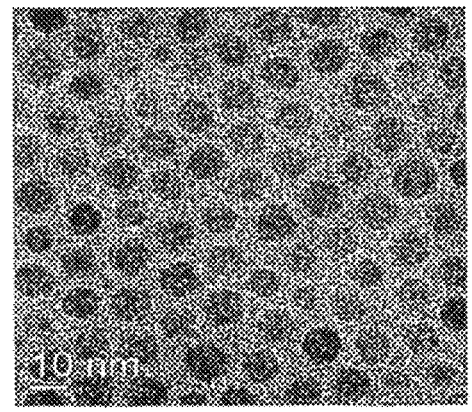
Figure 5:
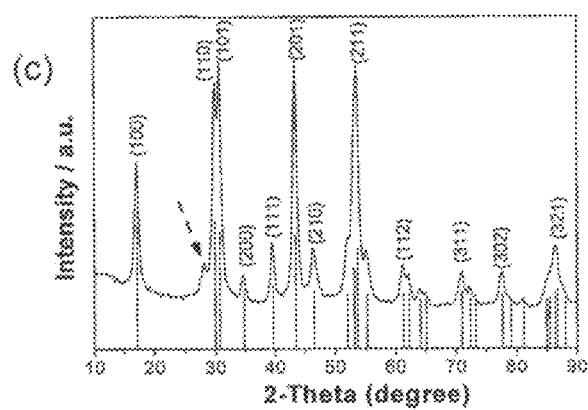
Figure 5:
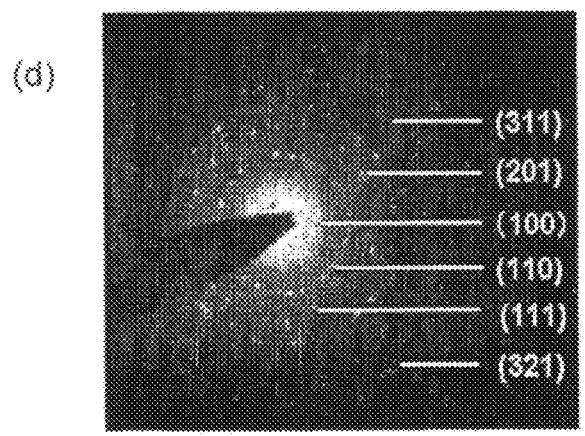

FIGS. 5a and 5b show TEM images of the $NaYF_4$:20% Yb,2% Er nanoparticles. The well-dispersed particles suggest that the long chain oleylamine ligand on the crystal surface prevented aggregation. The average diameter of the nanoparticles, obtained from measuring 200 particles randomly from 5 TEM micrographs, was 10.5 nm, with a standard derivation of ±0.7 nm. FIG. 5c shows that these nanoparticles were in hexagonal phase. The peak positions and intensities of these nanoparticles agreed well with calculated hexagonal $NaYF_4$:Yb,Er nanoparticles (line pattern in the lower part of FIG. 5c).

There were two unknown small peaks at 2θ~64° and 73°. There was a residual amount of cubic phase as indicated by the dashed arrow in FIG. 5c. Combined with the TEM results, the particles were confirmed to be single crystals. Similar TEM results were also observed for $NaYF_4$:20% Yb,2% Tm nanoparticles (results not shown).

The selected area electron diffraction (SAED) pattern (FIG. 5d) shows the polycrystalline diffraction rings corresponding to the (100), (110), (111), (201), (311) and (321) of the hexagonal $NaYF_4$ lattice. The SAED pattern as shown in FIG. 5d showed six of the diffraction rings corresponding to the hexagonal phase $NaYF_4$ nanoparticles.

Figure 6:
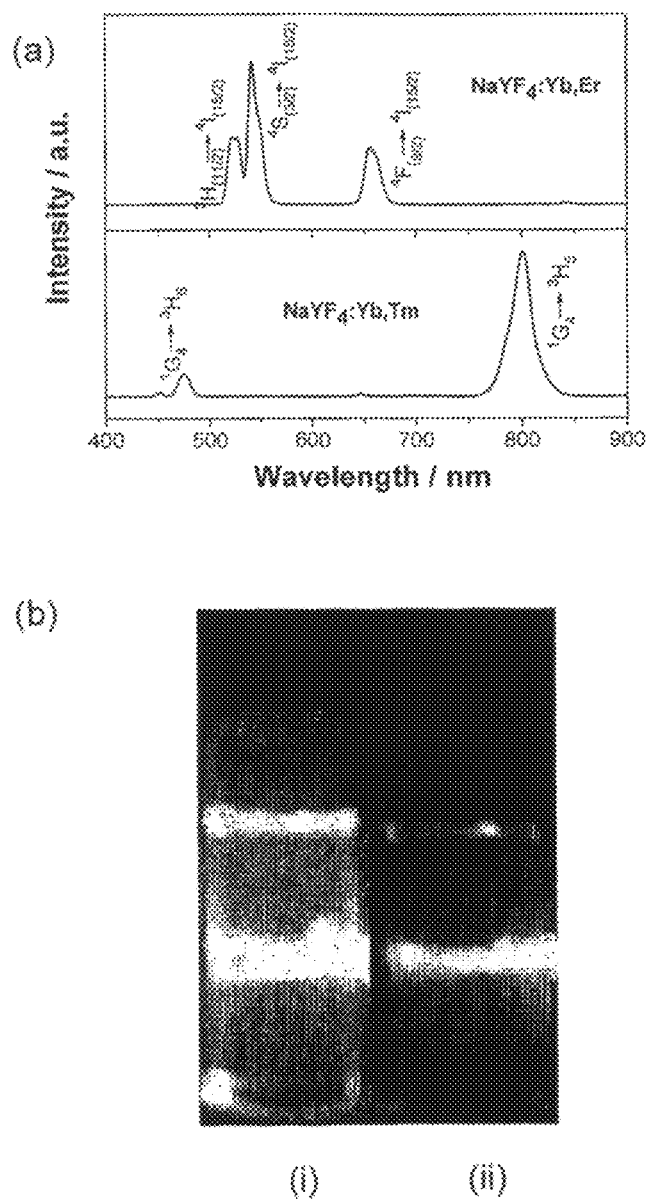
FIG. 6 shows (a) the fluorescence spectra and (b) fluorescence picture of the hexagonal phase (i) $NaYF_4$:Yb,Er and (ii) $NaYF_4$:Yb,Tm nanoparticles. The excitation is 980 nm NIR laser.

FIG. 6a shows the room-temperature up-conversion fluorescence spectra of the $NaYF_4$:20% Yb,2% Er and $NaYF_4$:20% Yb,2% Tm nanoparticles. For $NaYF_4$:20% Yb,2% Er nanoparticles, under 980 nm NIR excitation (continuous wave, CW), there were three emission peaks at 522.5, 541.5 and 655.5 nm, which were assigned to $^4H_{11/2}$ to $^4I_{15/2}$, $^4S_{3/2}$ to $^4I_{15/2}$ and $^4F_{9/2}$ to $^4I_{15/2}$ transitions of erbium, respectively (G S Yi et al, 2004). For $NaYF_4$:20% Yb,2% Tm nanoparticles, the blue emission band at 450.5 and 475 nm corresponded to the transitions from $^1G_4$ to $^3H_6$ and $^1G_4$ to $^3H_6$ of thulium, respectively (G S Yi and G M Chow, 2005). A strong near infrared emission at 801.5 nm was attributed to the transition from $^1G_4$ to $^3H_5$ (S Heer et al, 2003). As-synthesized $NaYF_4$:20% Yb,2% Er and $NaYF_4$:20% Yb,2% Tm nanoparticles were easily dispersed in organic solvents like hexane and formed a transparent colloidal solution. FIG. 6b (i) and (ii) show the $NaYF_4$:20% Yb,2% Er and $NaYF_4$:20% Yb,2% Tm nanoparticles colloidal solution (0.1 wt.-%) respectively under 980 nm NIR excitation (CW). The laser power for excitation was 1 W with a power density <0.1 $W/mm^2$. The bands of light in FIG. 6b(i) refer to the 522.5 nm and 541.5 nm emission of the $NaYF_4$:20% Yb,2% Er nanoparticles, while the bands of light in FIG. 6b(ii) corresponds to the 450.5 nm and 475 nm emission of the $NaYF_4$:20% Yb,2% Tm nanoparticles, respectively.

Example 1.2

Synthesis of Cubic Phase $NaYF_4$:Yb,Er and $NaYF_4$:Yb,Tm Nanoparticles

For the synthesis of cubic $NaYF_4$:20% Yb,2% Er and $NaYF_4$:20% Yb,2% Tm nanoparticles, a mixture of 2 mmol $CF_3COONa$, 0.78 mmol of $(CF_3COO)_3Y$, 0.2 mmol of $(CF_3COO)_3Yb$ and 0.02 mmol of $(CF_3COO)_3Er/(CF_3COO)_3Tm$ was dissolved in 10 ml of 1-octadecene, with 2 ml of oleic acid. The solution was passed through a 0.22 μm filter (Millipore) to remove any residue. Under vigorous stirring in a 50 ml flask, the mixture was heated to 300° C. in the presence of argon for protection from oxidation. After 1 h, heating was stopped. The transparent reaction mixture was allowed to cool to 80° C. before 20 ml of ethanol was added. The nanoparticles were isolated by centrifuging. They were washed 3 times with hexane and 3 times with de-ionized water to remove any NaF residue.

Figure 7:
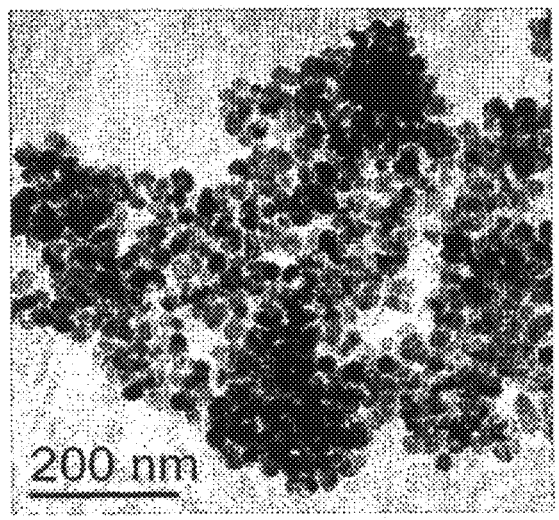
FIG. 7 shows (a) the TEM picture and (b) the XRD pattern of the cubic phase $NaYF_4$:Yb,Er and $NaYF_4$:Yb,Tm nanoparticles.
Figure 7:
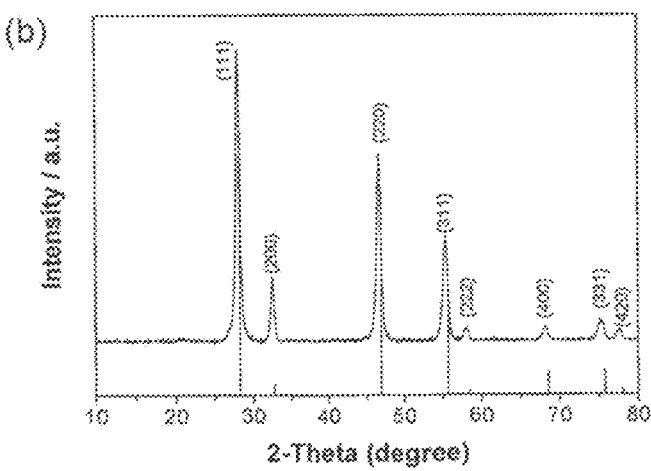

The average diameter of the nanoparticles obtained was 22 nm, with narrow size distribution, as shown in FIG. 7a. X-ray diffraction (XRD) results showed that these nanoparticles were in the cubic phase (see FIG. 7b). The up-conversion fluorescence of the nanoparticles obtained was 7.5 times lower than that of the hexagonal phase nanoparticles described in Example 1.1 above.

Example 1.3

Synthesis of Core and Core/Shell NaYF$_4$:Yb,Er/NaYF$_4$ and NaYF$_4$:Yb,Tm/NaYF$_4$ Nanoparticles For the synthesis of hexagonal NaYF$_4$:20% Yb,2% Er and NaYF$_4$:20% Yb,2% Tm core nanoparticles, a mixture of 0.5 mmol CF$_3$COONa, 0.195 mmol of (CF$_3$COO)$_3$Y, 0.05 mmol of (CF$_3$COO)$_3$Yb and 0.005 mmol of (CF$_3$COO)$_3$Er/(CF$_3$COO)$_3$Tm was dissolved in 5 ml oleylamine, and passed through a 0.22 µm filter (Millipore) to remove any residue. Under vigorous stirring in a 25 ml flask, the mixture was heated to 340° C. in the presence of argon protection to produce core nanoparticles. After 30 min, 0.5 ml of the core nanoparticle product was taken out for reference. 1 ml shell precursor solution containing 0.5 mmol of CF$_3$COONa and 0.25 mmol of (CF$_3$COO)$_3$Y in oleylamine was slowly added into the reaction. The reaction was allowed to continue for another 30 min. The reaction mixture was allowed to cool down to room temperature and kept as stock solution.

Figure 8:
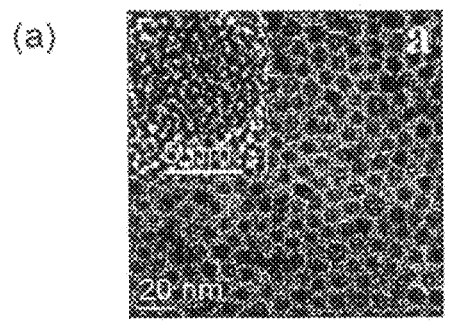
FIG. 8 shows (a) the TEM photographs of $NaYF_4$:Yb,Er core, (b) $NaYF_4$:Yb,Er(Tm)/$NaYF_4$ core/shell, and (c) XRD pattern of the core, core/shell nanoparticles.
Figure 8:
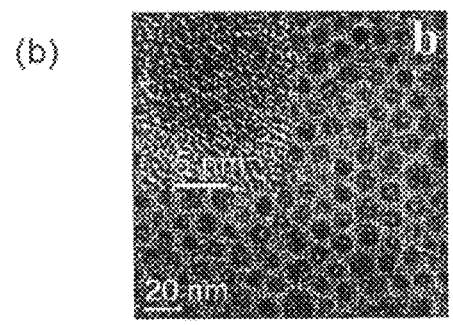
Figure 8:
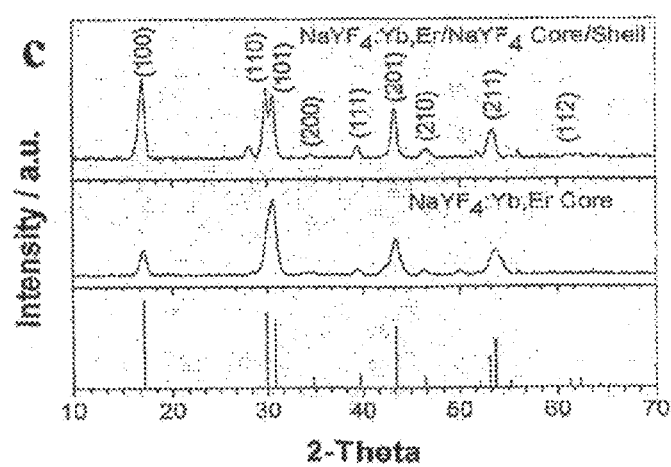
Figure 9:
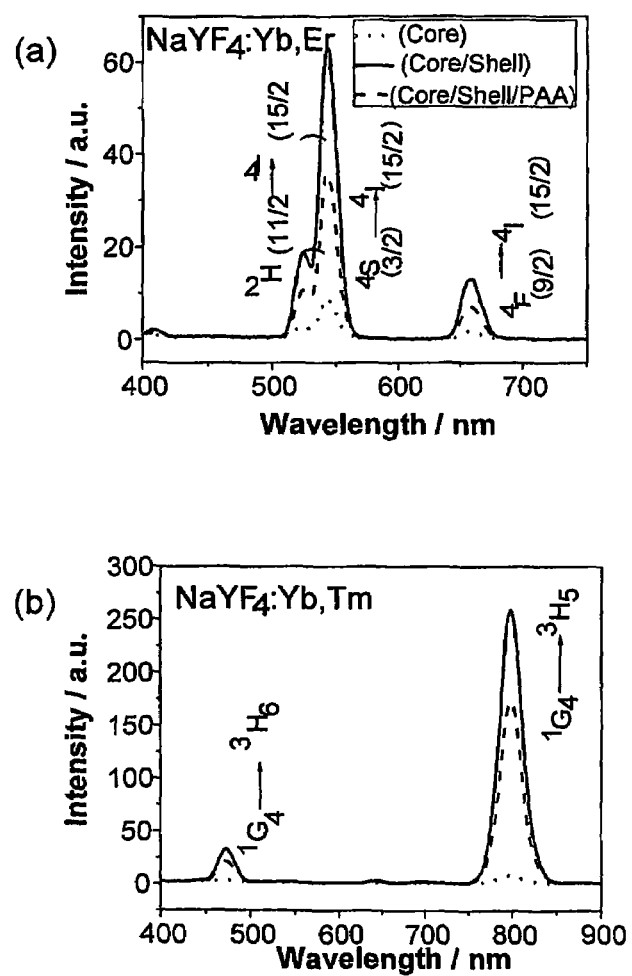
FIG. 9 shows (a) fluorescence spectra of core, core/shell and PAA coated core/shell $NaYF_4$:Yb,Er and (b) $NaYF_4$:Yb,Tm nanoparticles. The excitation is 980 nm NIR laser.
Figure 10:
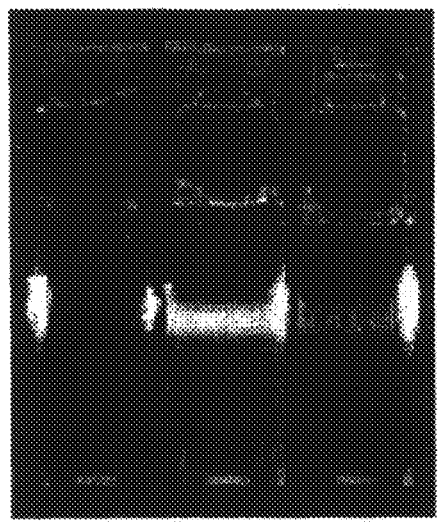
FIG. 10 shows (a) the fluorescence pictures of core, core/shell and PAA coated core/shell $NaYF_4$:Yb,Er and (b) $NaYF_4$:Yb,Tm nanoparticles. The excitation is 980 nm NIR laser.
Figure 10:
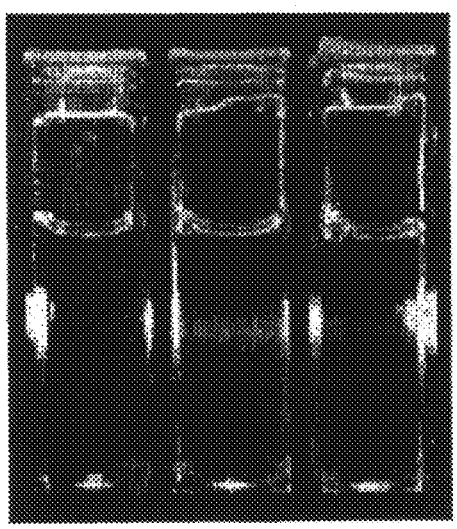

The average diameter of the core nanoparticles obtained was 8.5 nm with a standard derivation of ±0.8 nm (FIG. 8*a*). The diameter of the core-shell (CS) nanoparticles was 11.1±1.5 nm as shown in FIG. 8*b*. X-ray diffraction (XRD) results showed that these nanoparticles were in hexagonal phase (see FIG. 8*c*). The fluorescent intensity of the core-shell nanoparticles was much stronger than the core nanoparticles, as shown in FIGS. 9(*a*), 9(*b*), 10(*a*) and 10(*b*). In particular, the fluorescent intensity was 7.4 times stronger for NaYF$_4$:Yb,Er and 29.6 times for NaYF$_4$:Yb,Tm.

Example 1.4

Synthesis of LiYF$_4$ Nanoparticles 0.5 mmol of CF$_3$COOLi and 0.5 mmol of (CF$_3$COO)$_3$Y were dissolved in 10 ml of oleylamine, passed through a 0.22 µm filter (Millipore) to remove any residue. Under vigorous stirring in a 50 ml flask, 0.5 ml of CF$_3$COOH was added. The solution was heated to reflux (~343° C.) under the protection of dry argon gas. After 1 h, heating was stopped. The reaction mixture was allowed to cool down to 80° C. before 20 ml of ethanol was added. The nanoparticles were isolated by centrifuge, rinsed with ethanol, and then stored.

Figure 11:
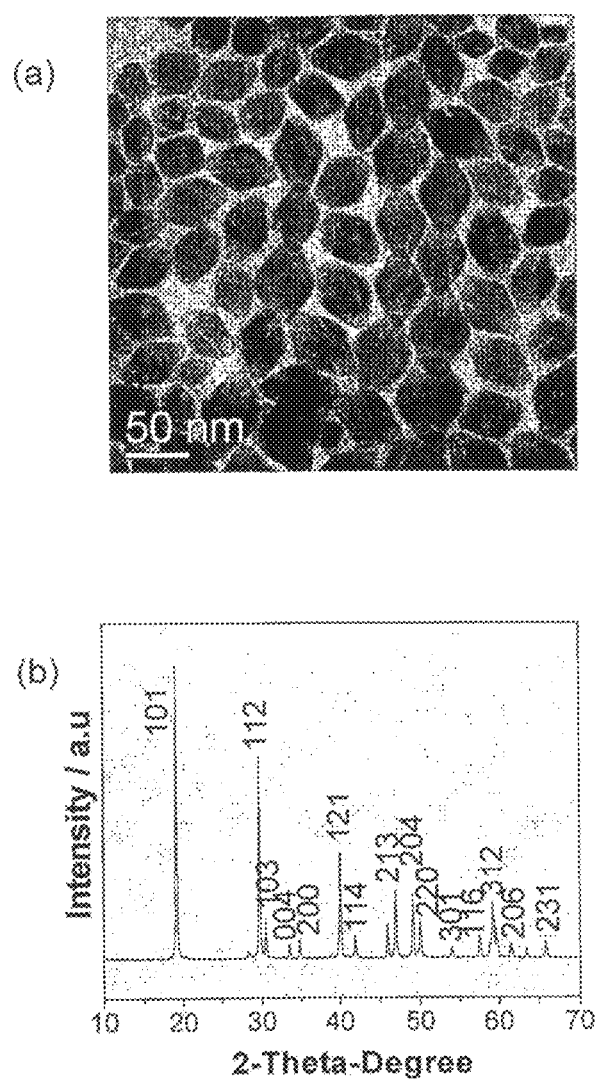
FIG. 11 shows (a) the TEM picture and (b) XRD pattern of $LiYF_4$ nanoparticles.

Most of the LiYF$_4$ particles took on rhombus shape, with equal side edge length of 49.3±4.5 nm, long axial length of 90.9±6.1 nm and short axial length of 51.4±3.3 nm, respectively (obtained from measuring 50 particles from 5 TEM micrographs). The obtuse angle between the two side edges was 130°. The nanoparticles were confirmed to be cuboid shape. The LiYF$_4$ nanoparticles were in tetragonal phase as shown in FIG. 11(*a*) with each particle as a single crystal (FIG. 11(*b*)).

Example 1.5

Synthesis of BaYF$_5$ Nanoparticles

Precursor of Ba(acac)$_2$ and (CF$_3$COO)$_3$Y were first dissolved in oleic acid in a separate vial (0.25 mmol/ml), and passed through a 0.22 µm filter (Millipore) to remove any of the residues. For the synthesis of BaYF$_5$ nanoparticles, 2 ml of Ba(acac)$_2$ and 2 ml of (CF$_3$COO)$_3$Y in oleic solution were introduced into 6 ml of octadecene. Under vigorous stirring in a 50 ml flask, the mixture was heated to 300° C. under the protection of dry argon gas. After 1 h, heating was stopped. The reaction mixture was allowed to cool down to 80° C. before 20 ml of ethanol was added. The nanoparticles were isolated by centrifuge, washing three times with ethanol, and stored.

Figure 12:
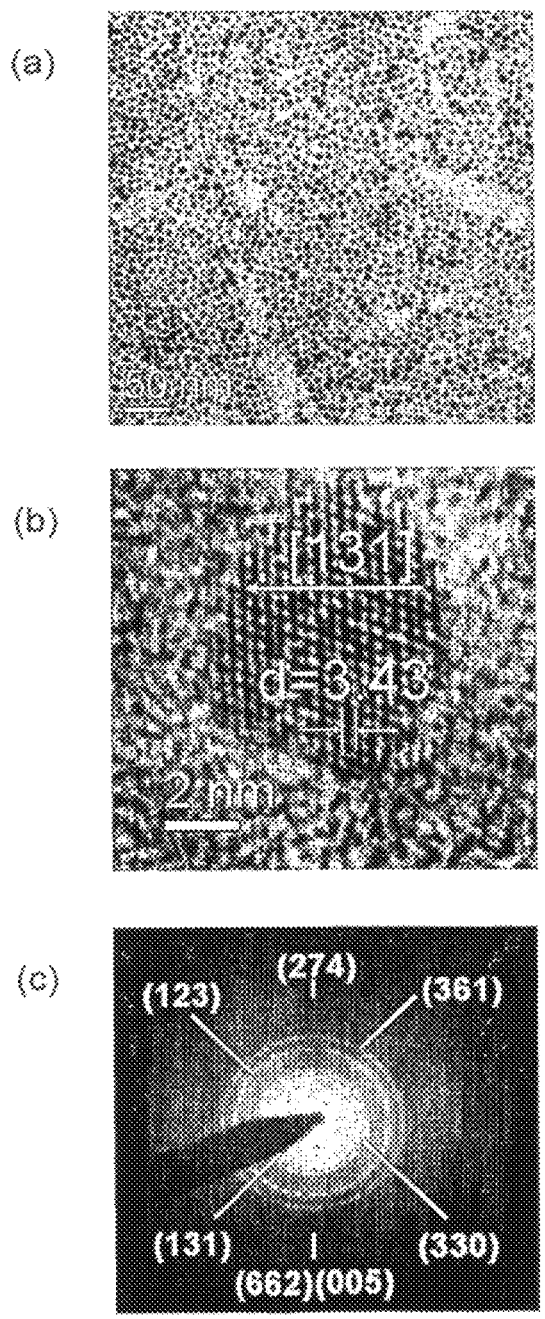
FIG. 12 shows (a) the TEM picture and (c) SAED pattern of $BaYF_5$ nanoparticles.
Figure 14:
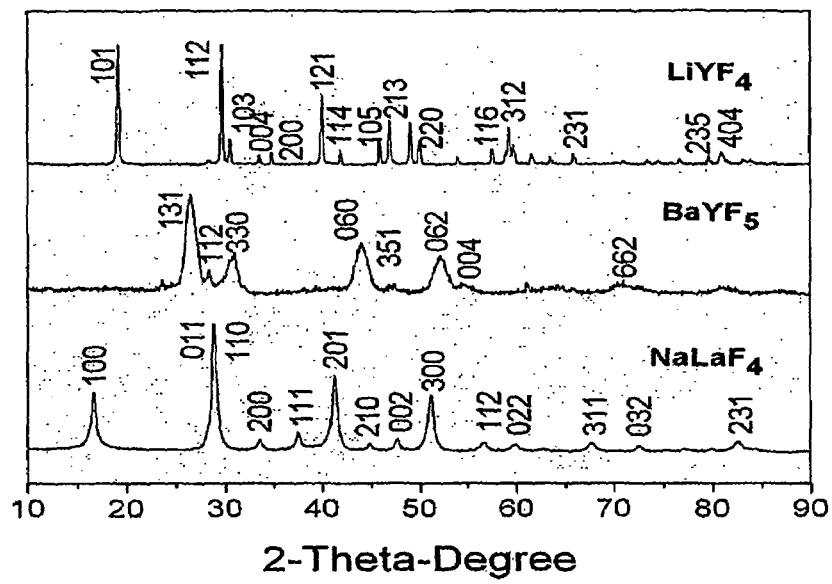
FIG. 14 shows the XRD patterns of $LiYF_4$, $BaYF_5$ and $NaLaF_4$ nanoparticles.

The average diameter of the BaYF$_5$ nanoparticles was 6.7±0.5 nm. XRD results confirmed that the BaYF$_5$ nanoparticles were real tetragonal phase crystals (FIG. 12 and FIG. 14).

Example 1.6

Synthesis of NaLaF$_4$ Nanoparticles 1 mmol of CF$_3$COONa and 0.5 mmol of (CF$_3$COO)$_3$La were dissolved in 10 ml of oleylamine, passed through a 0.22 µm filter (Millipore) to remove any residue. Under vigorous stirring in a 50 ml flask, 0.5 ml of CF$_3$COOH was added. The solution was heated to reflux (~345° C.) under the protection of dry argon gas. After 1 h, heating was stopped. The reaction mixture was allowed to cool down to 80° C. before 20 ml of ethanol was added. The nanoparticles were isolated by centrifuge, washed three times with hexane, and another 3 times with de-ionized water to remove any NaF residue.

Figure 13:
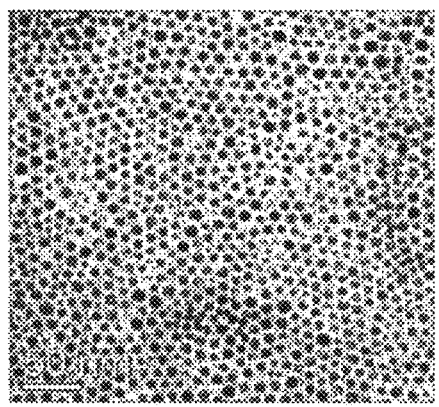
FIG. 13 shows (a) the TEM picture and (c) SAED pattern of $NaLaF_4$ nanoparticles.
Figure 13:
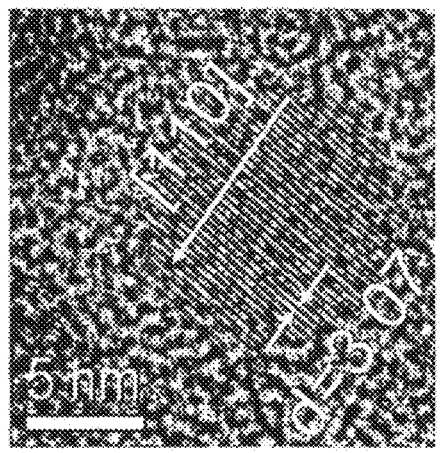
Figure 13:
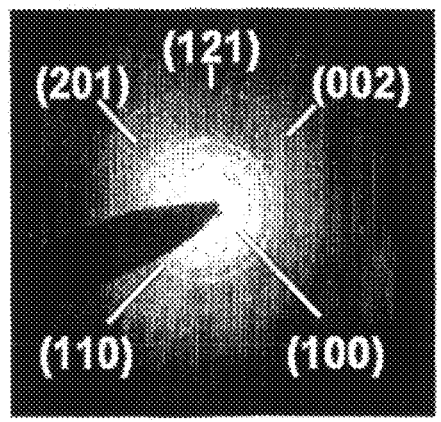

The average diameter of the NaLaF$_4$ nanoparticles was 8.8±1.2 nm. XRD results confirmed that the NaLaF$_4$ nanoparticles were real hexagonal phase crystals (FIG. 13 and FIG. 14).

Example 1.7

Figure 15:
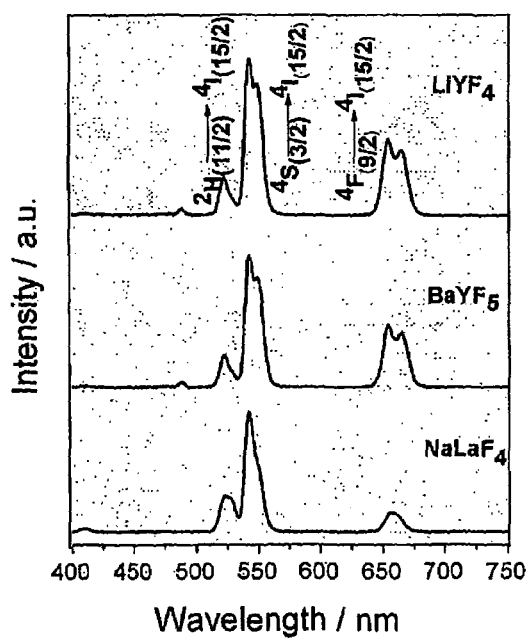
FIG. 15 shows the fluorescence spectra of Yb—Er co-doped $LiYF_4$, $BaYF_5$ and $NaLaF_4$ nanoparticles.

Synthesis of 20% Yb, 3% Er Co-Doped LiYF$_4$, BaYF$_5$ and NaLaF$_4$ Nanoparticles The synthesis procedure was the same as that used to prepare undoped LiYF$_4$, BaYF$_5$ and NaLaF$_4$ nanoparticles, except that 78% (CF$_3$COO)$_3$Y, 20% (CF3COO)$_3$Yb and 2% (CF$_3$COO)$_3$Er mixture was used as the rare earth source, instead of using a single source of (CF$_3$COO)$_3$Y for the synthesis of LiYF$_4$, BaYF$_5$ in examples 1.4 and 1.5 respectively. For the synthesis of doped NaLaF$_4$, 78% (CF$_3$COO)$_3$La, 20% (CF$_3$COO)$_3$Yb and 2% (CF$_3$COO)$_3$Er mixture were used instead of using single source of (CF$_3$COO)$_3$La as in example 1.6. The fluorescence spectra of the doped nanoparticles prepared is shown in FIG. 15.

Example 1.8

Synthesis of LaF$_3$ Nanoparticles 1 mmol of (CF$_3$COO)$_3$La was dissolved in 10 ml of oleylamine, and passed through a 0.22 µm filter (Millipore) to remove any residue. Under vigorous stirring in a 50 ml flask, the solution was heated to reflux (~345° C.) under the protection of dry argon gas. After 1 h, heating was stopped. The reaction mixture was allowed to cool down to 80° C. before 20 ml of ethanol was added. The nanoparticles were isolated by centrifuge, and washed three times with hexane.

Figure 16:
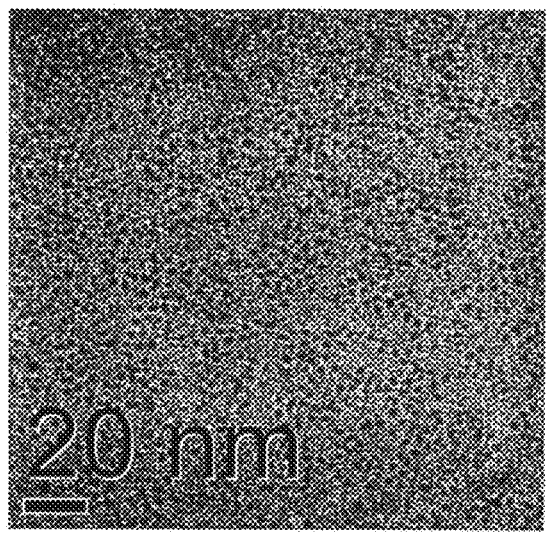
FIG. 16 shows the TEM picture of $LaF_3$ nanoparticles.

The average diameter of the LaF$_3$ nanoparticles obtained was 4.3 nm. XRD results confirmed that the LaF$_3$ nanoparticles were in the hexagonal phase (FIG. 16).

Example 1.9

Synthesis of YF$_3$ Nanoparticles 1 mmol of (CF$_3$COO)$_3$Y was dissolved in 10 ml of oleylamine, and passed through a 0.22 µm filter (Millipore) to remove any residue. Under vigorous stirring in a 50 ml flask, 0.5 ml of $CF_3COOH$ was added. The solution was heated to reflux (~345° C.) under the protection of dry argon gas. After 1 h, heating was stopped. The reaction mixture was allowed to cool down to 80° C. before 20 ml of ethanol was added. The nanoparticles were isolated by centrifuge, and washed three times with hexane.

Figure 17:
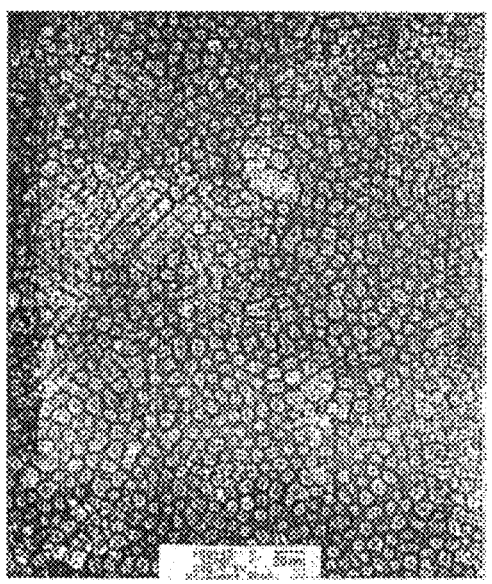
FIG. 17 shows the TEM picture of $YF_3$ nanoparticles.

The average diameter of the $YF_3$ nanoparticles obtained was 8.7 nm. XRD results confirmed that the $YF_3$ nanoparticles were in the tetragonal phase (FIG. 17).

Example 1.10

Synthesis of $NaYF_4$:20% Yb,2% Er Nanoparticles in Tetracosane with Trioctylphosphine (TOP) as Surfactant Synthesis of $NaYF_4$:20% Yb,2% Er nanoparticles was performed according to the following steps:
A) Preparation of $(CF_3COO)_3Y$, $(CF_3COO)_3Yb$, $(CF_3COO)_3Er$ and $CF_3COONa$
A rare earth chloride solution containing 0.78 mmol of $YCl_3$, 0.2 mmol of $YbCl_3$ and 0.02 mmol of $ErCl_3$ was mixed with 2 ml 25% ammonium hydroxide solution. White precipitates of rare earth hydroxide were then formed. They were separated by centrifugation, washed several times with de-ionized water. The precipitates were then mixed with 1 mmol (0.106 g) sodium carbonate ($Na_2CO_3$) and dissolved completely in 2 ml trifluoroacetic acid ($CF_3COOH$). After drying at 80° C. for 24 h, a mixture of $(CF_3COO)_3Y$, $(CF_3COO)_3Yb$, $(CF_3COO)_3Er$ and $CF_3COONa$ was obtained.
B) The mixture of $(CF_3COO)_3Y$, $(CF_3COO)_3Yb$, $(CF_3COO)_3Er$ and $CF_3COONa$ was dissolved in 4 ml of trioctylphosphine (TOP).
C) In a typical procedure for the synthesis of $NaYF_4$:20% Yb,2% Er nanoparticles, 6.4 g tetracosane was heated to 385° C. under argon protection. 2 ml (0.5 mmol) of the solution obtained in step B was quickly injected into it through a 5 ml syringe. A sudden decrease of temperature to 340° C. occurred.

Heating was restored to 360° C. and maintained for 30 min. After the reaction, the mixture was allowed to cool down to around 70° C. before adding 20 ml of hexane to dissolve tetracosane. $NaYF_4$:20% Yb,2% Er nanoparticles were collected by centrifugation. The product was washed several times with hexane and a white powder obtained was left to dry in open air at room temperature overnight.

The reaction can be illustrated as:

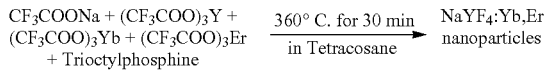

Figure 18:
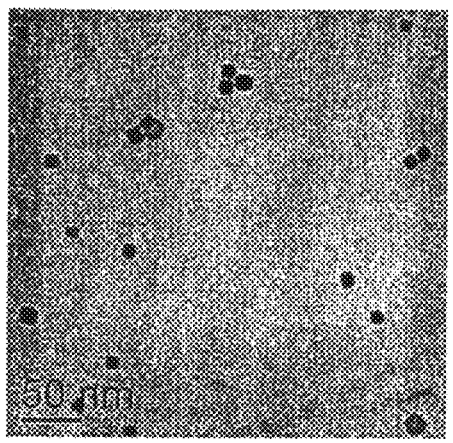
FIG. 18 shows (a) the TEM picture of the $NaYF_4$:20% Yb,2% Er nanoparticles, and (b) up-conversion fluorescence of the nanoparticles in hexane. The excitation is a 980 nm NIR laser with power density of 1 W.
Figure 18:
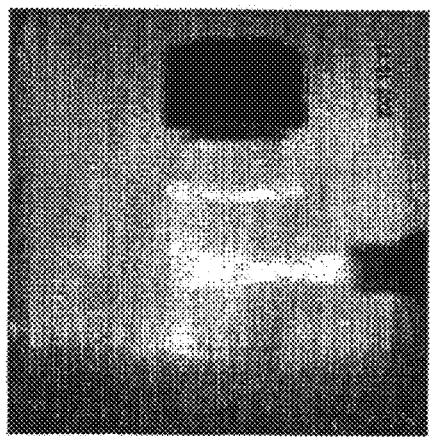

FIG. 18(*a*) shows the TEM picture of the $NaYF_4$:Yb,Er nanoparticles obtained and FIG. 18(*b*) shows the up-conversion fluorescence of the nanoparticles in hexane. The excitation was with NIR laser source at 980 nm with a power density of 1 W. Average size of the nanoparticles was 11 nm with narrow size distribution. Most of the nanoparticles were in the hexagonal phase.

Example 1.11

Figure 19:
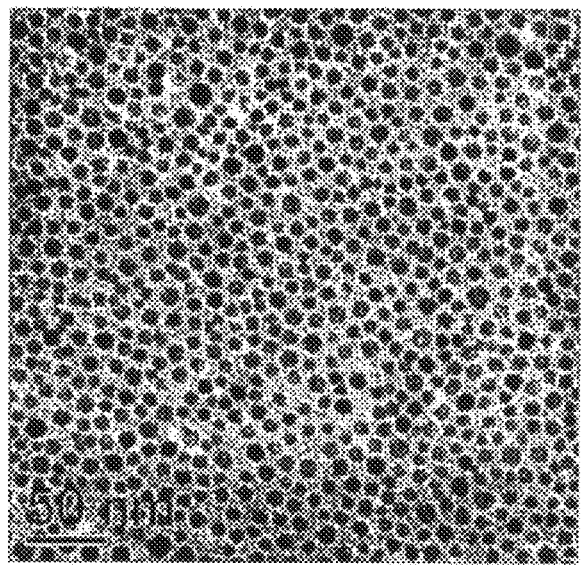
FIG. 19 shows the TEM picture of the $NaYF_4$:Yb,Er nanoparticles obtained in 1-octadecene with oleylamine as surfactant, at temperature of 300° C. for 1 h.

Synthesis of $NaYF_4$:20% Yb,2% Er Nanoparticles in Tetracosane with Oleylamine as Surfactant 6.4 g tetracosane was heated to 300° C. under argon protection. 0.5 mmol of $(CF_3COO)_3Y$, $(CF_3COO)_3Yb$, $(CF_3COO)_3Er$ and $CF_3COONa$ in 2 ml of oleylamine was quickly injected into it through a 5 ml syringe. After 1 h of reaction, the mixture was allowed to cool down to around 70° C. before adding 20 ml of hexane to dissolve tetracosane. $NaYF_4$:20% Yb,2% Er nanoparticles were collected by centrifugation. The product was washed several times with hexane and the white powder obtained was left to dry in open air at room temperature overnight. FIG. 19 shows the TEM picture of the $NaYF_4$:Yb,Er nanoparticles obtained. The average particle size was 9 nm. Most of the nanoparticles obtained were in the cubic phase.

Example 1.12

Figure 20:
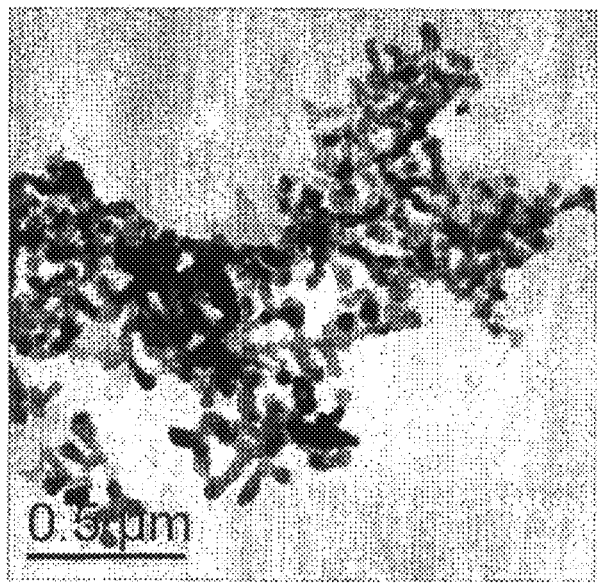
FIG. 20 shows the TEM picture of the $NaYF_4$:Yb,Er nanoparticles prepared in tetracosane with octadecaneamine as surfactant, at temperature of 340° C. for 30 min.

Synthesis of $NaYF_4$:20% Yb,2% Er Nanoparticles in Tetracosane with Octadecaneamine as Surfactant 6.4 g tetracosane was heated to 340° C. under argon protection. 0.5 mmol of $(CF_3COO)_3Y$, $(CF_3COO)_3Yb$, $(CF_3COO)_3Er$ and $CF_3COONa$ in 2 ml of octadecaneamine was added in. After 1 h reaction, the mixture was allowed to cool down to around 70° C. before adding 20 ml of hexane to dissolve tetracosane. $NaYF_4$:20% Yb,2% Er nanoparticles were collected by centrifugation. The product was washed several times with hexane and the white powder obtained was left to dry in open air at room temperature overnight. FIG. 20 is the TEM picture of the $NaYF_4$:Yb,Er nanoparticles obtained. Most of the nanoparticles were agglomerated and were in the hexagonal phase.

Example 2

Synthesis of Thin Films

Example 2.1

Synthesis of $NaYF_4$:Yb,Er Thin Film with Yellow Fluorescent Emission

Figure 21:
FIG. 21 shows the $NaYF_4$:Yb,Er thin film on glass substrates. Under 980 nm NIR excitation, green emission (as shown by arrow) was observed.

For the synthesis of $NaYF_4$:20% Yb,2% Er thin film, a mixture of 1 mmol $CF_3COONa$, 0.78 mmol of $(CF_3COO)_3Y$, 0.2 mmol of $(CF_3COO)_3Yb$ and 0.02 mmol of $(CF_3COO)_3Er$ was dissolved in butanol and water, and then passed through a 0.22 µm filter (Millipore) to remove any residue. The precursor was dipped onto a glass substrate. A spin-coater was used to spread the precursors on the glass substrate. After drying, it was sintered in an oven at 500° C. for 10 min to obtain the $NaYF_4$:20% Yb,2% Er thin film. Yellow emission was observed when excited with 980 nm NIR laser as shown by the arrow in FIG. 21.

Example 2.2

Synthesis of $NaYF_4$:Yb,Tm Thin Film with Blue Fluorescent Emission

For the synthesis of $NaYF_4$:20% Yb,2% Tm thin film, a mixture of 1 mmol $CF_3COONa$, 0.78 mmol of $(CF_3COO)_3Y$, 0.2 mmol of $(CF_3COO)_3Yb$ and 0.02 mmol of $(CF_3COO)_3Tm$ was dissolved in butanol and water, and then passed through a 0.22 µm filter (Millipore) to remove any residue. The precursor was dipped onto a glass substrate. A spin-coater was used to spread the precursors on the glass substrate. After drying, it was sintered in an oven at 500° C. under argon protection for 10 min to get the $NaYF_4$:20%Yb,2%Tm thin film. Blue emission was observed when excited with 980 nm NIR laser (result not shown).

Example 2.3

Synthesis of YOF:Yb,Er Thin Film with Red Fluorescent Emission

Figure 22:
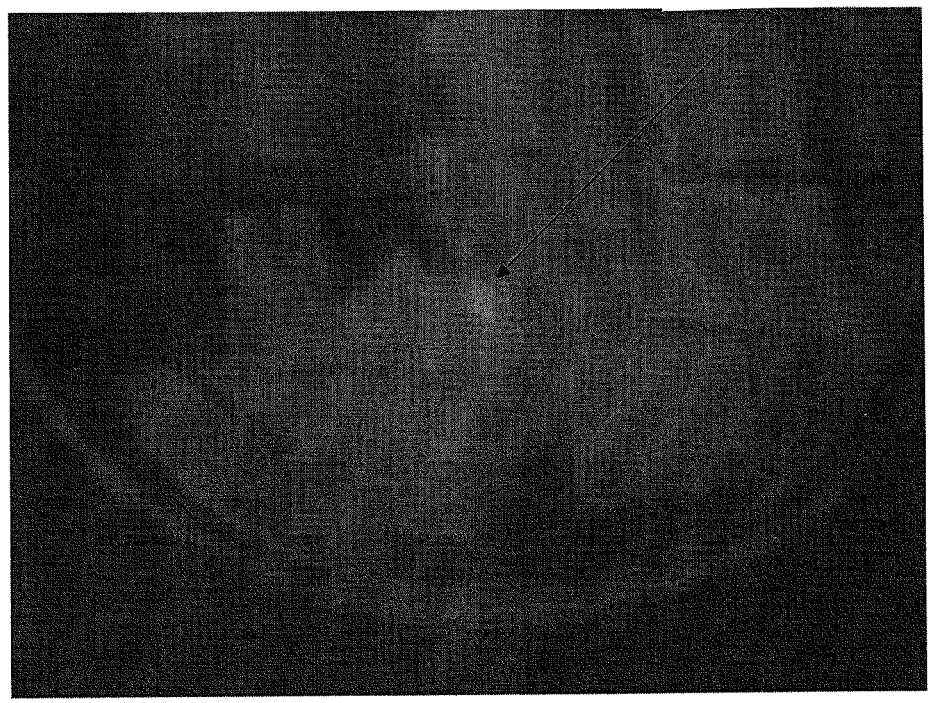
FIG. 22 shows YOF:Yb,Er thin film on glass substrates. Under 980 nm NIR excitation, red emission (as shown by arrow) was observed.

For the synthesis of YOF:20% Yb,2% Er thin film, a mixture of 0.78 mmol of $(CF_3COO)_3Y$, 0.2 mmol of $(CF_3COO)_3Yb$ and 0.02 mmol of $(CF_3COO)_3Er$ was dissolved in butanol and water, and then passed through a 0.22 μm filter (Millipore) to remove any residue. The precursor was dipped onto a glass substrate. A spin-coater was used to spread the precursors on the glass substrate. After drying, it was sintered in an oven at 500° C. under argon protection for 10 min to get the YOF:20% Yb,2% Er thin film. Red emission was observed when excited with 980 nm NIR laser, as shown by the arrow in FIG. 22.

Example 2.4

Synthesis of $NaYF_4$:Yb,Er Thin Film without Using Solvent

For the synthesis of $NaYF_4$:20% Yb,2% Er thin film, a powder mixture of 1 mmol $CF_3COONa$, 0.78 mmol of $(CF_3COO)_3Y$, 0.2 mmol of $(CF_3COO)_3Yb$ and 0.02 mmol of $(CF_3COO)_3Er$ was pressed onto a glass substrate. It was sintered in an oven at 500° C. for 10 min to get the $NaYF_4$: 20% Yb,2% Er film. Bright green fluorescence was observed when excited with a 980 nm NIR laser (result not shown).

Example 3

Synthesis of Water-Soluble Nanoparticles

The nanoparticles obtained by the methods of Example 1 may be made water-soluble through surface modification of the nanoparticles by surface exchange of, replacement of or attachment by a water soluble molecule. Two methods are described in the examples below.

Example 3.1

Synthesis of Water Soluble $NaYF_4$:Yb,Er and $NaYF_4$:Yb,Tm Nanoparticles by Surface Exchange The As-synthesized hydrophobic $NaYF_4$:Yb,Er and $NaYF_4$:Yb,Tm nanoparticles with oleylamine surfactant or shell on their surface as described in Example 1.3, were modified to have a hydrophilic surface by replacing oleyamine on the particles' surface with a bipolar regent, polyethylene glycol 600 (HOOC-PEG-COOH). 10 mg of the prepared nanoparticles in 1 ml hexane and 10 mg of the ligand to be exchanged in 1 ml of ethanol were mixed and vortexed for 48 h. After surface exchange, the nanoparticles remained as a clear colloid in deionized water, without any noticeable settling or precipitation after two weeks.

Example 3.2

Synthesis Water Soluble $NaYF_4$:Yb,Er and $NaYF_4$:Yb,Tm Nanoparticles by Surface Exchange The As-prepared hydrophobic $NaYF_4$:Yb,Er(Tm) nanoparticles were transformed into hydrophilic nanoparticles by replacing the oleylamine on the nanoparticles' surface with a bipolar surfactant, 11-aminoundecanoic acid (AUA). The modification of the nanoparticles was achieved by dispersing them with AUA in boiling 0.1 mol/L NaOH. The product, after surfactant exchange, was clear and stable colloidal in deionized water or Tris buffer.

Example 3.3

Synthesis Water Soluble PAA (Poly Acrylic Acid) Coated $NaYF_4$:Yb,Er and $NaYF_4$:Yb,Tm Nanoparticles 100 μl each of the core and core-shell (CS) nanoparticles stock solutions as described in Example 1.3 were taken into two centrifuge tubes. The core and CS nanoparticles were precipitated by centrifugation. The supernatant was discarded, and the nanoparticles were rinsed twice with ethanol, dispersed in 4 ml of chloroformed. A second solution of 50 mg PAA (poly acrylic acid) polymer in 2 ml chloroform was then added. The chloroform was slowly evaporated via vacuum, and the residue was dissolved in 5 ml of ethanol or water, resulting in an optically clear solution. The obtained nanoparticles had the structure as shown in FIG. 3(a).

Figure 23:
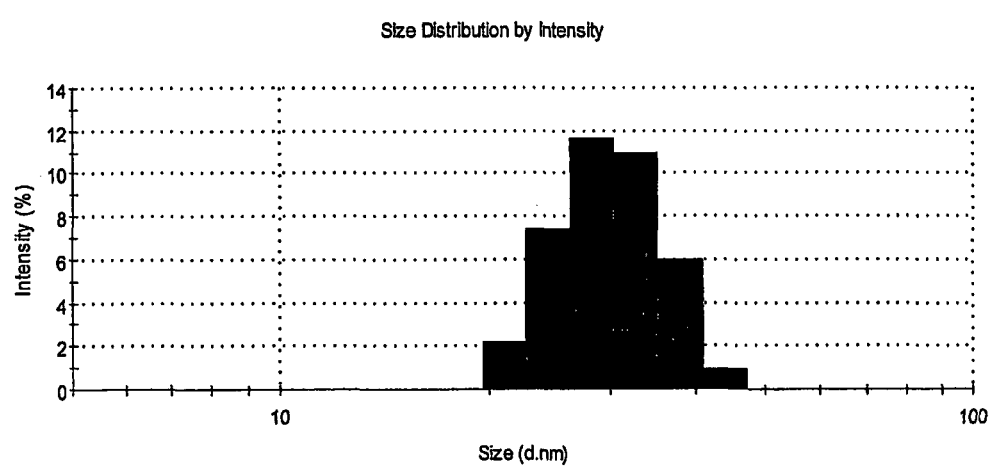
FIG. 23 shows the size distribution of the PAA polymer coated $NaYF_4$:Yb,Er/$NaYF_4$ nanoparticles, obtained from the dynamic light scattering technique.

The diameter of the PAA coated nanoparticles was obtained via a dynamics light scattering technique using a dynamic light scattering instrument (Nano-ZS from Malvern Instruments). The diameter of the obtained nanoparticles were 30.2±5.24 nm (FIG. 23).

Example 3.4

Synthesis Water Soluble PEG-Phospholipid Coated $NaYF_4$:Yb,Er and $NaYF_4$:Yb,Tm Nanoparticles 1,2-Distearoyl-sn-Glycero-3-Phosphoethanolamine-N-[Methoxy(Polyethylene glycol)-2000] (Ammonium Salt), also called 18:0 PEG2 PE, may be used as a surface coating to make the nanoparticles of the present invention water soluble. Its structure is as seen in FIG. 4a.

100 μL of $NaYF_4$:Yb,Er and NaYF4:Yb,Tm core-shell nanoparticles as described in Example 1.3, were precipitated with ethanol and dried under vacuum. The nanoparticles were then suspended in 2 mL chloroform with 20 mg of phospholipids. After complete evaporation of the chloroform, the residue was heated at 80° C. and 1 mL of water was added to obtain an optically clear suspension containing PEG-PE micelles.

Since this suspension contained both empty micelles and those containing nanoparticles, the empty micelles were removed with centrifugation. The micelles containing nanoparticles formed a pellet while the empty micelles stayed suspended. The supernatant was discarded and the nanoparticles-micelles were re-suspended in water. This can be illustrated as seen in FIG. 3.

Example 3.5

Synthesis Water Soluble PEG-Phospholipid Coated $NaYF_4$:Yb,Er and $NaYF_4$:Yb,Tm Nanoparticles with Functional Groups Such as —COOH and -Biotin The procedure is similar to that described in Example 3.4, except that a mixture of 18:0 PEG2 PE and PEG2PE carboxylic acid (or biotin, or amino) was used, instead of single 18:0 PEG2 PE. Their structures are as shown in FIGS. 4a and 4b respectively.

Example 4

Conjugation of Biomolecules with Fluorescent Nanoparticles

For the methods under Example 4, the core-shell (CS) nanoparticles obtained by the method in Example 1.3 were used.

Example 4.1

Conjugation of NaYF$_4$:Yb,Er and NaYF$_4$:Yb,Tm Nanoparticles with Streptavidin Conjugation of PAA coated nanoparticles (with carboxylic acid group) with streptavidin was obtained by EDC (1-ethyl-3-(3-dimethylamino propyl)carbodiimide)-mediated coupling. The CS nanoparticles were dissolved in 10 mM sodium phosphate, pH 7.4. 10 mg streptavidin was added to the nanoparticles suspension followed by 10 mg EDC per milliliter of the nanoparticle/streptavidin mixture. The carbodiimide was made soluble using a vortex mixer and allowed to react for 2 h at room temperature. The conjugate was then purified by gel filtration using a column of Sephadex G-75.

Example 4.2

Conjugation of NaYF$_4$:Yb,Er and NaYF$_4$:Yb,Tm Nanoparticles with Antibody Conjugation of nanoparticle-micelles (with carboxylic groups on them) with antibody was performed using a method similar to that for obtaining PAA-coated nanoparticles. A carboxyl-PEG-DSPE was incorporated in the CS nanoparticles during preparation. It was then activated with water-soluble carbodiimide (EDC) in the presence of N-hydroxysulfosuccinimide in mildly acidic pH, and the desired antibody added in mildly alkaline HEPES buffer.

Example 4.3

Conjugation of NaYF$_4$:Yb,Er and NaYF$_4$:Yb,Tm Nanoparticles with DNA

Conjugation of CS nanoparticle-micelles with DNA was obtained by replacing 20% of the mPEG-2000 PE with an amino PEG-PE. DNA contains a disulfide group at the 5' end. This disulfide bonds were cleaved with dithiothreitol (DTT) and the oligonucleotide was purified of excess DTT. The DNA was then coupled to the QD-micelle using Sulfosuccinimidyl 4-(N-maleimidomethyl)cyclohexane-1-carboxylate.

Example 5

Effect of Temperature

Figure 24:
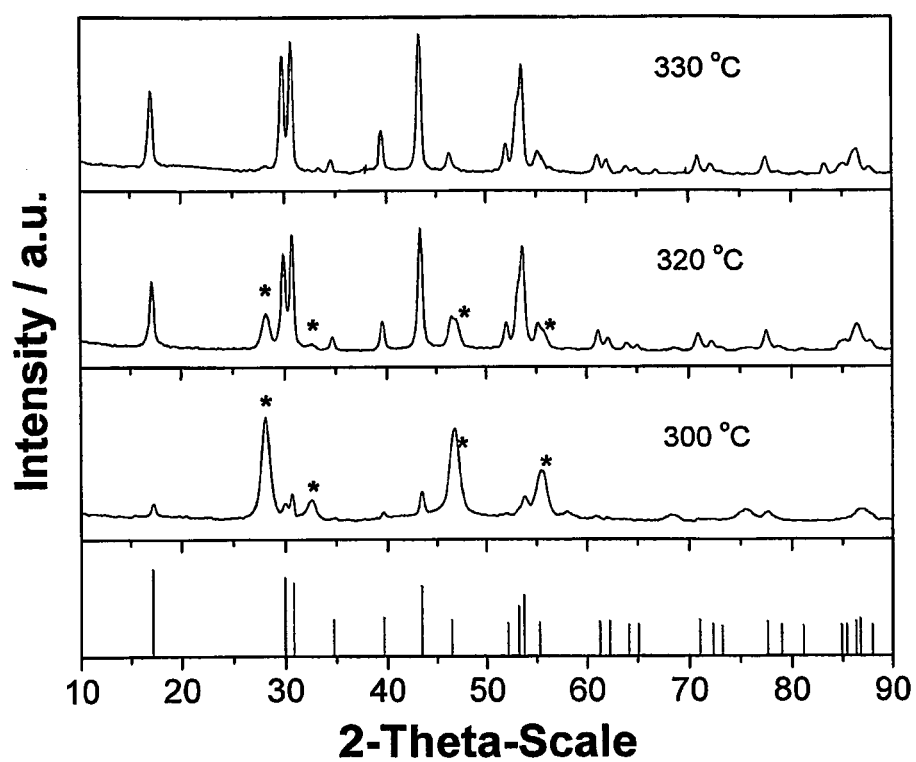
FIG. 24 shows XRD patterns of the $NaYF_4$:20% Yb,2% Er nanoparticles synthesized at 300° C., 320° C. and 330° C., respectively, in oleylamine for 1 h. The particles in cubic phase are peaks marked with asterisk. The line pattern in the lower part is the calculated hexagonal phase of $NaYF_4$.

The reaction temperature plays an important role in the synthesis of hexagonal phase NaYF$_4$ nanoparticles. FIG. 24 shows the XRD patterns of the NaYF$_4$:20% Yb,2% Er nanoparticles synthesized in a 1 h reaction at 300° C., 320° C. and 330° C., respectively. At 300° C., 80% of the nanoparticles were in the cubic phase (peaks marked with asterisk) with the remaining in hexagonal phase. At 320° C., the intensity of hexagonal phase significantly increased. At 330° C., nearly all the nanoparticles were in the hexagonal phase. Corresponding sharp up-conversion fluorescence enhancement was observed with increasing temperature in synthesis of nanoparticles. The line pattern in the lower part of FIG. 24 shows the calculated hexagonal phase of NaYF$_4$.

Example 6

Effect of Solvent

Figure 25:
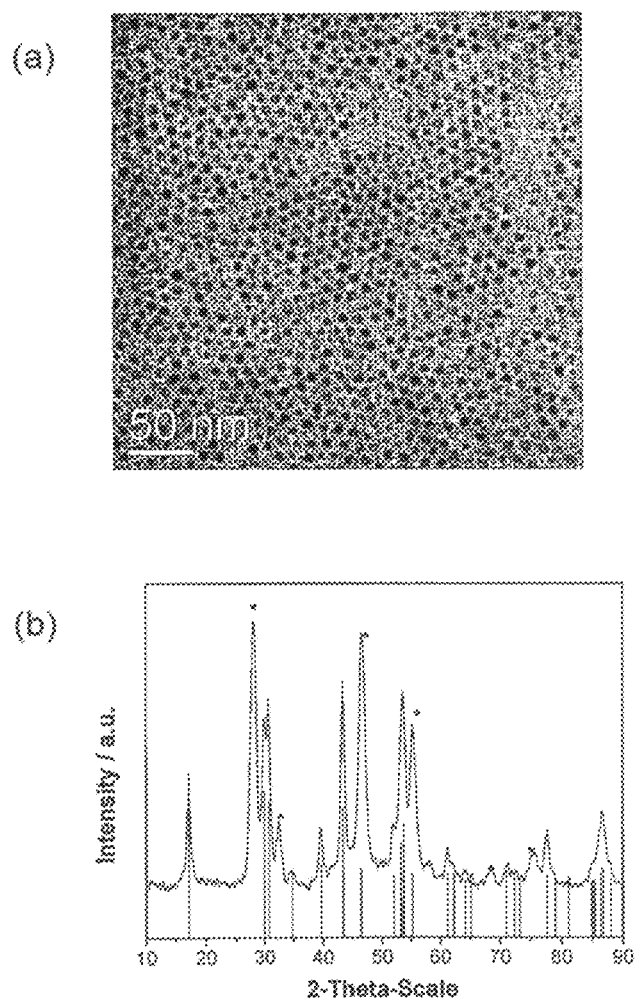
FIG. 25 shows (a) TEM image of $NaYF_4$:Yb,Er nanoparticles prepared in 2 ml oleic acid and 8 ml oleylamine solution at 330° C. for 1 h, and (b) shows the XRD pattern of dominant cubic phase (marked with asterisk) and hexagonal phase. The line pattern in (b) is the calculated hexagonal phase of $NaYF_4$.

Oleylamine, simultaneously as ligand and solvent, was critical in controlling the formation and size of hexagonal phase NaYF$_4$ nanoparticles. Hexagonal NaYF$_4$ nanoparticles, as the major phase, were synthesized with 10 ml of oleylamine. However, when a mixture of 8 ml oleylamine and 2 ml oleic acid was used as ligand/solvent at 330° C. for 1 h, mono-dispersed NaYF$_4$:20% Yb,2% Er nanoparticles with a smaller size of 8 nm were obtained. However, most of particles were in the cubic phase, as shown in FIGS. 25 (*a*) and (*b*). In the absence of oleylamine, when 2 ml of oleic acid was used as ligand and 8 ml non-chelating 1-octadecene as solvent, only cubic NaYF$_4$:Yb,Er nanoparticles with much larger size (~28 nm) were synthesized (FIGS. 7 (*a*) and (*b*)). The fluorescence efficiency of these larger cubic NaYF$_4$:Yb, Er nanoparticles, synthesized $\geq$300° C. was still 7.5 times smaller than that of hexagonal nanoparticles. Differential thermal analysis of the precursors in oleylamine confirmed the onset of a phase transition at 310° C., consistent with the XRD results of formation of hexagonal phase. No such phase transition was observed for the precursors in oleic acid.

Discussion

In summary, infrared-to-visible up-conversion fluorescent nanoparticles, in particular, hexagonal phase NaYF$_4$:20% Yb,2% Er and NaYF$_4$:20% Yb,2% Tm were synthesized by decomposition of multi-precursors of CF$_3$COONa, (CF$_3$COO)$_3$Y, (CF$_3$COO)$_3$Yb and (CF$_3$COO)$_3$Er/(CF$_3$COO)$_3$Tm in oleylamine at 330° C. The average particle size was 10.5 nm with a narrow size distribution of ±0.7 nm. Green or blue emission was observed by doping with Er or Tm, respectively, even with only a 5 mW, 980 nm laser pointer. These small nanoparticles were easily dispersed in organic solvents producing a transparent colloidal solution. The up-conversion fluorescence intensity of the hexagonal nanoparticles was high compared to other cubic nanoparticles. In particular, the fluorescence intensity far exceeded that of As-synthesized cubic NaYF$_4$:Yb,Er (37 nm) nanoparticles that required subsequent high temperature annealing to achieve the hexagonal phase transformation (G S Yi et al, 2004). These features of the nanoparticles may be exploited for application as bio-probes.

Compared to corresponding bulk phosphors (prepared using hydrothermal method), the up-conversion fluorescence output as determined by the integrated intensity of the emission peak of the nanoparticles was smaller by one order of magnitude. The decrease of up-conversion fluorescence have been reported and studied previously for Y$_2$O$_2$S:Yb,Er up-conversion phosphors (X Y Chen et al, 2003). When the size of the Y$_2$O$_2$S:Yb,Er phosphors decreased to 30 nm, the up-conversion efficiency was reduced to be about 22% of their bulk counterparts. When the size decreased from 30 nm to 2 nm, the efficiency rapidly reduced. The decrease in fluorescence efficiency was attributed to the lack of low frequency phonon modes and restricted excitation migration in nano-phosphors. The reduction of up-conversion fluorescence was also attributed to the organic ligand on the surface that quenched the ions for fluorescence (S Heer et al, 2004; S Heer et al, 2003).

The invention claimed is:

1. A method of preparing at least one nano-structured material of formula $M_1M_2X_t$ comprising the step of heating:
   at least one compound having the formula $[CX_3(CX_2)_n(CH_2)_mCOO]_pM_1$; and
   at least one compound having the formula $[CX_3(CX_2)_n(CH_2)_mCOO]_pM_2$;
   wherein
      each X is the same or different and is selected from the group consisting of: halogens, O, S, Se, Te, N, P and As;
      $0 < t \leq 10$;
      each n is the same or different and is $0 \leq n \leq 10$;
      each m is the same or different and is $0 \leq m \leq 10$;
      each p is the same or different and is $1 \leq p \leq 5$;
      each $M_1$ is the same or different and is selected from the group consisting of: Li, Na, K, Rb, Cs, Fr, Be, Mg, Ca, Sr, Ba, Ra and $NH_4$;
      each $M_2$ is the same or different and is selected from the group consisting of: Sc, Y, La, Ce, Pr, Nd, Pm, Sm, Eu, Gd, Tb, Dy, Ho, Er, Tm, Yb and Lu.

2. The method according to claim 1, wherein the method further comprises heating at least one compound having a formula $[CX_3(CX_2)_n(CH_2)_mCOO]_pM_q$ with the least one compound having a formula $[CX_3(CX_2)_n(CH_2)_mCOO]_pM_1$ and the at least one compound having a formula $[CX_3(CX_2)_n(CH_2)_mCOO]_pM_2$ to prepare at least one nano-structured material of formula $M_1M_2X_t:M_q$, wherein
   each $M_q$ is the same or different and is selected from the group consisting of Sc, Y, La, Ce, Pr, Nd, Pm, Sm, Eu, Gd, Tb, Dy, Ho, Er, Tm, Yb and Lu; and
   each q is the same or different and is $1 \leq q \leq 10$.

3. The method according to claim 1, wherein $M_2$ is selected from the group consisting of: transition metal ions, inner transition metal ions, and Group I to Group VI metal ions.

4. The method according to claim 1, wherein the heating is carried out in the presence of at least one polar or non-polar solvent, or a mixture thereof.

5. The method according to claim 1, wherein the nano-structured material is selected from the group consisting of: $NaM_2F_4$, $LiM_2F_4$, $KM_2F_4$, $RbM_2F_4$, $CsM_2F_4$, $BeM_2F_5$, $Be(M_2)_2F_8$, $MgM_2F_5$, $Mg(M_2)_2F_8$, $CaM_2F_5$, $Ca(M_2)_2F_8$, $SrM_2F_5$, $Sr(M_2)_2F_8$, $BaLnF_5$, $Ba(M_2)_2F_8M_2F_3$,
wherein each $M_2$ is the same or different and is selected from the group consisting of: Sc, Y, La, Ce, Pr, Nd, Pm, Sm, Eu, Gd, Tb, Dy, Ho, Er, Tm, Yb and Lu.

6. The method according to claim 5, wherein the nano-structured material is $NaYF_4$.

7. The method according to claim 2, wherein the nano-structured material is selected from the group consisting of:
$NaM_2F_4:M_q$, $LiM_2F_4:M_q$, $KM_2F_4:M_q$, $RbM_2F_4:M_q$, $CsM_2F_4:M_q$, $BeM_2F_5:M_q$, $Be(M_2)_2F_8:M_q$, $MgM_2F_5:M_q$, $Mg(M_2)_2F_8:M_q$, $CaM_2F_5:M_q$, $Ca(M_2)_2F_8:M_q$, $SrM_2F_5:M_q$, $Sr(M_2)_2F_8:M_q$, $BaLnF_5:M_q$, and $Ba(M_2)_2F_8M_2F_3:M_q$,
wherein each $M_2$ is the same or different and is selected from the group consisting of: Sc, Y, La, Ce, Pr, Nd, Pm, Sm, Eu, Gd, Tb, Dy, Ho, Er, Tm, Yb and Lu and each $M_q$ is the same or different and is selected from the group consisting of Yb, Er, Tm and Ho.

8. The method according to claim 7 wherein the nano-structured material is $NaYF_4$:Yb,Tm or $NaYF_4$:Yb,Ho.

9. The method according to claim 2, wherein the at least one compound of formula $[CX_3(CX_2)_n(CH_2)_mCOO]_pM_1$ is selected from the group consisting of: $CF_3COONa$ and $CF_3COOLi$;
   the at least one compound of formula $[CX_3(CX_2)_n(CH_2)_mCOO]_pM_2$ is selected from the group consisting of: $(CF_3COO)_3Y$ and $(CF_3COO)_3La$; and
   the at least one compound of formula $[CX_3(CX_2)_n(CH_2)_mCOO]_pM_q$ is selected from the group consisting of: $(CF_3COO)_3Yb$, $(CF_3COO)_3Er$, $(CF_3COO)_3Tm$ and $(CF_3COO)_3Ho$.

10. The method according claim 1, wherein the nano-structured material has a structure selected from the group consisting of: hexagonal, cubic, tetragonal, rhombohedral, orthorhombic, monoclinic, triclinic and a combination thereof.

11. The method according to claim 1, wherein the nano-structured material comprises at least one dimension of size <50 nm.

12. The method according to claim 1, wherein the nano-structured material is in the form of nanoparticles, and the nanoparticle is in the form of a core nanoparticle, and the method further comprises applying at least one organic and/or inorganic material on the core, to obtain a core-shell nanoparticle(s).

13. The method according to claim 12, wherein the shell material has the formula $M_1M_2X_t$ or $M_1M_2X_t:M_q$, wherein
   each X is the same or different and is selected from the group consisting of: halogens, O, S, Se, Te, N, P and As;
   each $M_1$ is selected from the group consisting of: Li, Na, K, Rb, Cs, Fr, Be, Mg, Ca, Sr, Ba, Ra and $NH_4$;
   each $M_2$ is selected from the group consisting of: Sc, Y, La, Ce, Pr, Nd, Pm, Sm, Eu, Gd, Tb, Dy, Ho, Er, Tm, Yb and Lu;
   each $M_q$ is selected from the group consisting of Sc, Y, La, Ce, Pr, Nd, Pm, Sm, Eu, Gd, Tb, Dy, Ho, Er, Tm, Yb and Lu;
   $0 < t \leq 10$; and
   $1 \leq q \leq 10$.

14. The method according to claim 1, wherein the nano-structured material is hexagonal phase $NaYF_4$.

15. The method according to claim 2, wherein the nano-structured material is hexagonal phase $NaYF_4$:Yb,Er, hexagonal phase $NaYF_4$:Yb,Tm or hexagonal phase $NaYF_4$:Yb,Ho.

16. The method according to claim 1, wherein the surface of the nano-structured material is modified by adding at least one surfactant, lipid, polymer, inorganic material, or a mixture thereof.

17. The method according to claim 16, wherein the at least one surfactant has Formula (I):

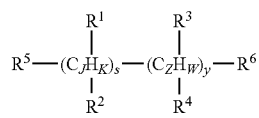

(Formula I)

wherein each J is the same or different, and $1 \leq J \leq 9$;

each K is the same or different, and $0 \leq K \leq 9$;

each s is the same or different, and $0 \leq s \leq 9$;

each Z is the same or different, and $1 \leq Z \leq 9$;

each W is the same or different, and $0 \leq W \leq 9$;

each y is the same or different, and $0 \leq y \leq 9$;

each $R^1$, $R^2$, $R^3$, $R^4$ and $R^5$ is the same or different, and is independently selected from the group consisting of: H, substituted or unsubstituted $C_1$-$C_6$ alkyl, substituted or unsubstituted $C_1$-$C_6$ aryl, HS, COOH, $NH_2$ and OH;

each $R_6$ is the same or different, and is selected from the group consisting of: COOH, $NH_2$, OH, P=O and P;

with the proviso that s+y<10.

* * * * *

UNITED STATES PATENT AND TRADEMARK OFFICE
CERTIFICATE OF CORRECTION

PATENT NO. : 8,435,472 B2  
APPLICATION NO. : 12/087414  
DATED : May 7, 2013  
INVENTOR(S) : Yi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1339 days.

Signed and Sealed this  
Eighth Day of September, 2015

Michelle K. Lee  
*Director of the United States Patent and Trademark Office*